(12) United States Patent  (10) Patent No.: US 9,876,174 B2
Wu et al.  (45) Date of Patent: Jan. 23, 2018

(54) ELECTRONIC DEVICE INCLUDING A FLUORANTHENE DERIVATIVE

(71) Applicant: E I DU PONT DE NEMOURS AND COMPANY, Wilmington, DE (US)

(72) Inventors: Weishi Wu, Landenberg, PA (US); Weiying Gao, Landenberg, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 15/472,680

(22) Filed: Mar. 29, 2017

(65) Prior Publication Data

US 2017/0200900 A1 Jul. 13, 2017

Related U.S. Application Data

(63) Continuation of application No. 15/031,031, filed as application No. PCT/US2014/060342 on Oct. 14, 2014.

(Continued)

(51) Int. Cl.
*H01L 51/00* (2006.01)
*C07D 239/26* (2006.01)
(Continued)

(52) U.S. Cl.
CPC .......... *H01L 51/0054* (2013.01); *C07C 13/66* (2013.01); *C07D 235/08* (2013.01);
(Continued)

(58) Field of Classification Search
None
See application file for complete search history.

(56) References Cited

U.S. PATENT DOCUMENTS

| 7,488,856 B2 | 2/2009 | Schwalm et al. |
| 2005/0067955 A1 | 3/2005 | Cho |

(Continued)

FOREIGN PATENT DOCUMENTS

| JP | 2010245062 A | 10/2010 |
| KR | 10-2011-0137897 | * 12/2011 |
| KR | 1020110137897 | 12/2011 |

OTHER PUBLICATIONS

Machine English translation of Cho et al. (KR 10-2011-0137897). Jun. 23, 2017.*

(Continued)

*Primary Examiner* — J. L. Yang

(57) ABSTRACT

There is provided a compound having Formula I. In Formula I: $R^3$-$R^{16}$ are the same or different and are H, D, alkyl, silyl, aryl, deuterated alkyl, deuterated silyl, or deuterated aryl, where no more than two $R^1$-$R^{16}$ are biphenyl and where at least two of $R^1$-$R^{16}$ have Formula II. In Formula II: Ar is phenyl, naphthyl, heteroaryl, spirofluorenyl, or a deuterated analog thereof; $R^{11}$ is the same or different at each occurrence and is D, alkyl, silyl, aryl, deuterated alkyl, deuterated silyl, or deuterated aryl, where adjacent $R^{11}$ groups can join to form a fused aromatic ring or fused deuterated aromatic ring; m is an integer form 0-4; n is an integer from 1-5; and the asterisk represents a point of attachment.

Formula I (Continued)

-continued

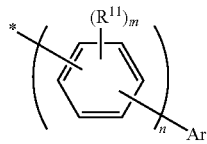

Formula II

19 Claims, 2 Drawing Sheets

Related U.S. Application Data

(60) Provisional application No. 61/895,497, filed on Oct. 25, 2013.

(51) Int. Cl.
| | |
|---|---|
| *C07C 13/66* | (2006.01) |
| *C09K 11/02* | (2006.01) |
| *C09K 11/06* | (2006.01) |
| *H05B 33/14* | (2006.01) |
| *C07D 235/08* | (2006.01) |
| *C07D 235/14* | (2006.01) |
| *C07D 403/14* | (2006.01) |
| *C07D 307/91* | (2006.01) |
| *H01L 51/50* | (2006.01) |

(52) U.S. Cl.
CPC ......... *C07D 235/14* (2013.01); *C07D 239/26* (2013.01); *C07D 307/91* (2013.01); *C07D 403/14* (2013.01); *C09K 11/025* (2013.01); *C09K 11/06* (2013.01); *H01L 51/0058* (2013.01); *H01L 51/0067* (2013.01); *H01L 51/5036* (2013.01); *H05B 33/14* (2013.01); *C07C 2103/18* (2013.01); *C07C 2103/40* (2013.01); *C07C 2603/18* (2017.05); *C07C 2603/40* (2017.05); *C09K 2211/1007* (2013.01); *C09K 2211/1011* (2013.01); *C09K 2211/1029* (2013.01); *C09K 2211/1044* (2013.01); *C09K 2211/1088* (2013.01); *C09K 2211/1092* (2013.01); *H01L 51/5012* (2013.01); *H01L 51/5016* (2013.01); *H01L 51/5072* (2013.01); *H01L 2251/5384* (2013.01)

(56) References Cited

U.S. PATENT DOCUMENTS

| | | | |
|---|---|---|---|
| 2005/0116626 A1* | 6/2005 | Cheng | ................ C07F 15/0033 313/504 |
| 2007/0063189 A1 | 3/2007 | Schwalm | |
| 2009/0110956 A1 | 4/2009 | Begley | |
| 2009/0230852 A1 | 9/2009 | Lee | |
| 2010/0252819 A1 | 10/2010 | Lecloux | |
| 2010/0253209 A1 | 10/2010 | Spindler | |
| 2011/0315965 A1 | 12/2011 | Takashima | |

OTHER PUBLICATIONS

Machine English Translation of KR10-2011-0137897. Date Published: Dec. 12, 2016.Applicant: Alpha Chem Co. Ltd., Inventor: Chol et al.
International Search Report of International Application No. PCT/US2014/060342. International Filing Date: Oct. 14, 2014. Publication No. WO2015061074. Publication Date: Apr. 30, 2015. International Search Report dated Jan. 8, 2015.

* cited by examiner

ELECTRONIC DEVICE INCLUDING A FLUORANTHENE DERIVATIVE

CROSS-REFERENCE TO RELATED APPLICATION

This application is a continuation of U.S. patent application Ser. No. 15/031,031, filed Apr. 21, 2016, which is hereby incorporated by reference in its entirety.

BACKGROUND INFORMATION

Field of the Disclosure

This disclosure relates in general to electroactive pyrimidine compounds. It also relates to organic electronic devices including at least one layer having a pyrimidine derivative.

Description of the Related Art

In organic photoactive electronic devices, such as organic light emitting diodes ("OLED"), that make up OLED displays, the organic electroactive layer is sandwiched between two electrical contact layers in an OLED display. In an OLED, the organic photoactive layer emits light through the light-transmitting electrical contact layer upon application of a voltage across the electrical contact layers.

It is well known to use organic electroluminescent compounds as the electroactive component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode. Charge transport materials can also be used as hosts in combination with the photoactive materials.

There is a continuing need for new materials for electronic devices.

SUMMARY

There is provided a fluoranthene derivative having Formula I

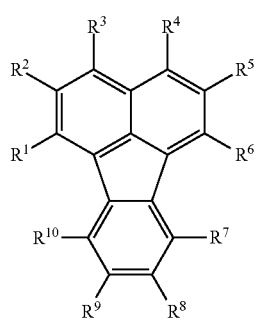

Formula I wherein:
  $R^1$-$R^{10}$ are the same or different and are selected from the group consisting of H, D, alkyl, silyl, aryl, deuterated alkyl, deuterated silyl, and deuterated aryl;

with the proviso that no more than one of $R^1$-$R^{10}$ is biphenyl and at least two of $R^1$-$R^{10}$ have Formula II

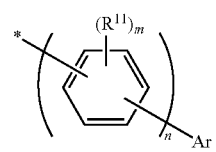

Formula II wherein:
  Ar is the same or different at each occurrence and is selected from the group consisting of phenyl, naphthyl, heteroaryl, spirofluorenyl, and deuterated analogs thereof;
  $R^{11}$ is the same or different at each occurrence and is selected from the group consisting of D, alkyl, silyl, aryl, deuterated alkyl, deuterated silyl, and deuterated aryl, wherein adjacent $R^{11}$ groups can join to form a fused aromatic ring or fused deuterated aromatic ring;
  m is an integer from 0-4;
  n is an integer from 1-5; and
  * represents a point of attachment.

There is also provided a compound having Formula III

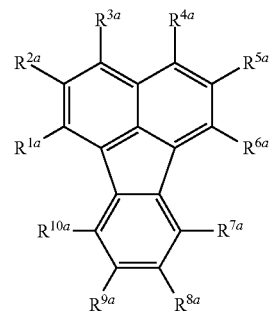

Formula III wherein:
  $R^{1a}$-$R^{10a}$ are the same or different and are selected from the group consisting of H, D, alkyl, silyl, aryl, deuterated alkyl, deuterated silyl, and deuterated aryl;
with the proviso that at least one of $R^{1a}$-$R^{10a}$ includes a spirofluorene group or deuterated analog thereof.

There is also provided a composition comprising (a) a host compound having Formula I or Formula III and (b) a dopant capable of electroluminescence having an emission maximum between 380 and 750 nm.

There is also provided an electronic device comprising at least one layer comprising the compound of Formula I or Formula III.

There is also provided an electronic device comprising at least one electroactive layer positioned between two electrical contact layers, wherein the at least one electroactive layer of the device includes an electroactive compound having Formula I or Formula III.

There is also provided an organic electronic device comprising an anode, a hole transport layer, a photoactive layer, an electron transport layer, and a cathode, wherein at least one of the photoactive layer and the electron transport layer includes a compound having Formula I or Formula III.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
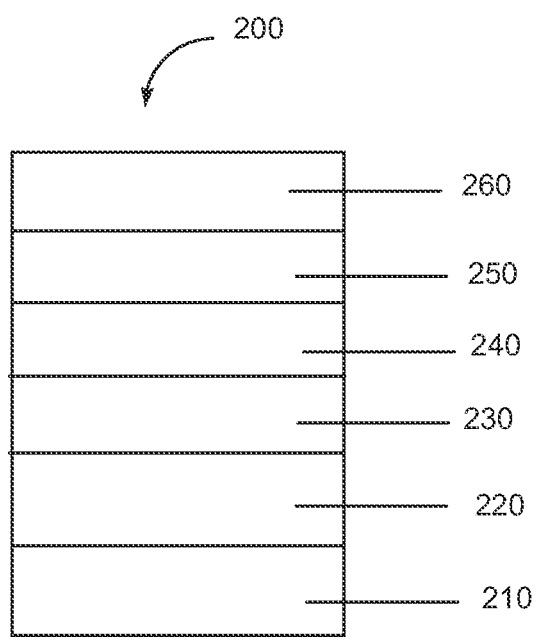
FIG. 1 includes a schematic diagram of another example of an organic electronic device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Fluoranthene Derivatives, the Electroactive Composition, the Electronic Device, and finally Examples.

1. Definitions and Clarification of Terms

Before addressing details of embodiments described below, some terms are defined or clarified.

The term "alkyl" is intended to mean a group derived from an aliphatic hydrocarbon. In some embodiments, alkyl groups have 1-20 carbons.

The term "aryl" is intended to mean a group derived from an aromatic compound. The term "aromatic compound" is intended to mean an organic compound including at least one unsaturated cyclic group having delocalized pi electrons. The term is intended to encompass both hydrocarbon aromatic compounds having only carbon and hydrogen atoms, and heteroaromatic compounds wherein one or more of the carbon atoms within the cyclic group has been replaced by another atom, such as nitrogen, oxygen, sulfur, or the like. In some embodiments, hydrocarbon aryl groups have 6-60 ring carbons. In some embodiments, heterocyclic aryl groups have 3-60 ring carbons.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport material facilitate negative charge. Although photoactive materials may also have some charge transport properties, the term "charge transport layer, material, member, or structure" is not intended to include a layer, material, member, or structure whose primary function is light emission or light reception.

The term "deuterated" is intended to mean that at least one hydrogen has been replaced by deuterium (abbreviated herein as "D"). The term "deuterated analog" refers to a structural analog of a compound or group in which one or more available hydrogens have been replaced with deuterium. In a deuterated compound or deuterated analog, the deuterium is present in at least 100 times the natural abundance level. In some embodiments, the compound is at least 10% deuterated. By "% deuterated" or "% deuteration" is meant the ratio of deuterons to the sum of protons plus deuterons, expressed as a percentage.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electroactive" when referring to a layer or material, is intended to mean a layer or material that exhibits electronic or electro-radiative properties. In an electronic device, an electroactive material electronically facilitates the operation of the device. Examples of electroactive materials include, but are not limited to, materials which conduct, inject, transport, or block a charge, where the charge can be either an electron or a hole, and materials which emit radiation or exhibit a change in concentration of electron-hole pairs when receiving radiation. Examples of inactive materials include, but are not limited to, insulating materials and environmental barrier materials.

The term "emission maximum" is intended to refer to the wavelength corresponding to the highest intensity of radiation emitted.

The term "fluorenyl" refers to a group containing the unit

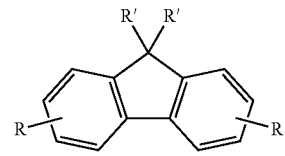

where R represents one or more groups which can be H, D, alkyl, aryl, or a point of attachment, and R' represents alkyl or aryl.

The term "charge injection," when referring to a layer, material, member, or structure, is intended to mean such layer, material, member or structure promotes charge migration into an adjacent layer, material, member or structure. Hole injection promotes the migration of positive charge. Electron injection promotes the migration of negative charge.

The term "host material" is intended to mean a material, usually in the form of a layer, to which a dopant may or may not be added. The host material may or may not have electronic characteristic(s) or the ability to emit, receive, or filter radiation.

The term "hydrocarbon aryl" is intended to mean an aryl group containing only hydrogen and carbon atoms.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

The terms "N-heterocycle" and "N-heteroaryl" refer to a heteroaromatic compound or heteroaromatic group, respectively, having at least one nitrogen in an aromatic ring.

The terms "O-heterocycle" and "O-heteroaryl" refer to a heteroaromatic compound or heteroaromatic group, respectively, having at least one oxygen in an aromatic ring.

The term "N,O,S-heterocycle" refers to a heteroaromatic compound or group having at least one heteroatom in an aromatic ring, where the heteroatom is N, O, or S. The N,O,S-heterocycle may have more than one type of heteroatom.

The term "organic electronic device," or sometimes just "electronic device," is intended to mean a device including one or more organic semiconductor layers or materials.

The term "photoactive" is intended to mean a material or layer that emits light when activated by an applied voltage (such as in a light emitting diode or chemical cell) or responds to radiant energy and generates a signal with or without an applied bias voltage (such as in a photodetector).

The terms "S-heterocycle" and "S-heteroaryl" refer to a heteroaromatic compound or heteroaromatic group, respectively, having at least one sulfur in an aromatic ring.

Unless otherwise indicated, all groups can be unsubstituted or substituted. Unless otherwise indicated, all groups can be linear, branched or cyclic, where possible. In some embodiments, the substituents are selected from the group consisting of alkyl, alkoxy, aryl, silyl, and deuterated analogs thereof.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic, and semiconductive member arts.

2. Fluoranthene Derivatives

Electron transport materials have been used as host materials in photoactive layers and in electron transport layers. Electron transport materials based on metal complexes of quinoline ligands, such as with Al, Ga, or Zr, have been used in these applications. However, there are several disadvantages. The complexes can have poor atmospheric stability when used as hosts. It is difficult to plasma clean fabricated parts employing such metal complexes. The low triplet energy leads to quenching of phosphorescent emission of >2.0 eV energy. In some embodiments, the fluoranthene derivatives described herein have higher triplet energies. As used herein, the term "fluoranthene derivative" is intended to mean a compound having at least one substituted fluoranthene group structure within the compound.

In some embodiments, the fluoranthene derivatives are useful as solution processable electron dominated hosts for OLED devices or as electron transport materials suitable for n-doping in OLED devices having a thick electron transport layer. In some embodiments, devices made with the fluoranthene derivatives have lower operating voltage, higher efficiency and longer lifetimes. In some embodiments, the materials are useful in any printed electronics application including photovoltaics and TFTs.

In some embodiments, the compound having Formula I is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

The fluoranthene derivative compounds described herein have Formula I

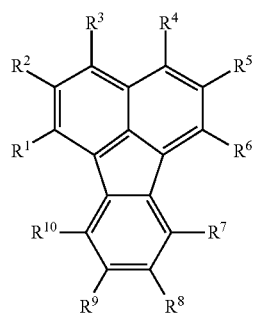

Formula I wherein:
R¹-R¹⁰ are the same or different and are selected from the group consisting of H, D, alkyl, silyl, aryl, deuterated alkyl, deuterated silyl, and deuterated aryl;
with the proviso that no more than one of R¹-R¹⁰ is biphenyl and at least two of R¹-R¹⁰ have Formula II

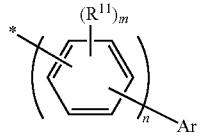

Formula II wherein:
Ar is the same or different at each occurrence and is selected from the group consisting of phenyl, naphthyl, heteroaryl, spirofluorenyl, and deuterated analogs thereof;
R¹¹ is the same or different at each occurrence and is selected from the group consisting of D, alkyl, silyl, aryl, deuterated alkyl, deuterated silyl, and deuterated aryl, wherein adjacent R¹¹ groups can join to form a fused aromatic ring or fused deuterated aromatic ring;
m is an integer from 0-4;
n is an integer from 1-5; and
* (the asterisk) represents the point of attachment to the fluoranthene core group.

In Formula I, no more than one of R¹-R¹⁰ is biphenyl.
In some embodiments of Formula I, none of R¹-R¹⁰ is biphenyl.
In some embodiments of Formula I, Ar is selected from the group consisting of phenyl, naphthyl, and deuterated analogs thereof.
In some embodiments of Formula I, Ar is selected from the group consisting of phenyl, naphthyl, and deuterated analogs thereof and n is 2.
In some embodiments of Formula I, Ar is an N-heteroaryl group or deuterated N-heteroaryl group having at least one ring atom which is N.
In some embodiments, the N-heteroaryl group is selected from the group consisting of pyrrole, pyridine, pyrimidines, triazine, diazole, benzodiazole, carbazole, imidazole, benzimidazole, imidazolobenzimidazole, triazole, benzotriazole, triazolopyridine, indolocarbazole, phenanthroline, quinoline, isoquinoline, quinoxaline, substituted derivatives thereof, and deuterated analogs thereof.
In some embodiments, the N-heteroaryl or deuterated N-heteroaryl is selected from the group consisting of

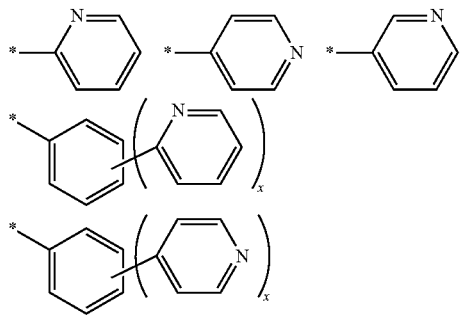

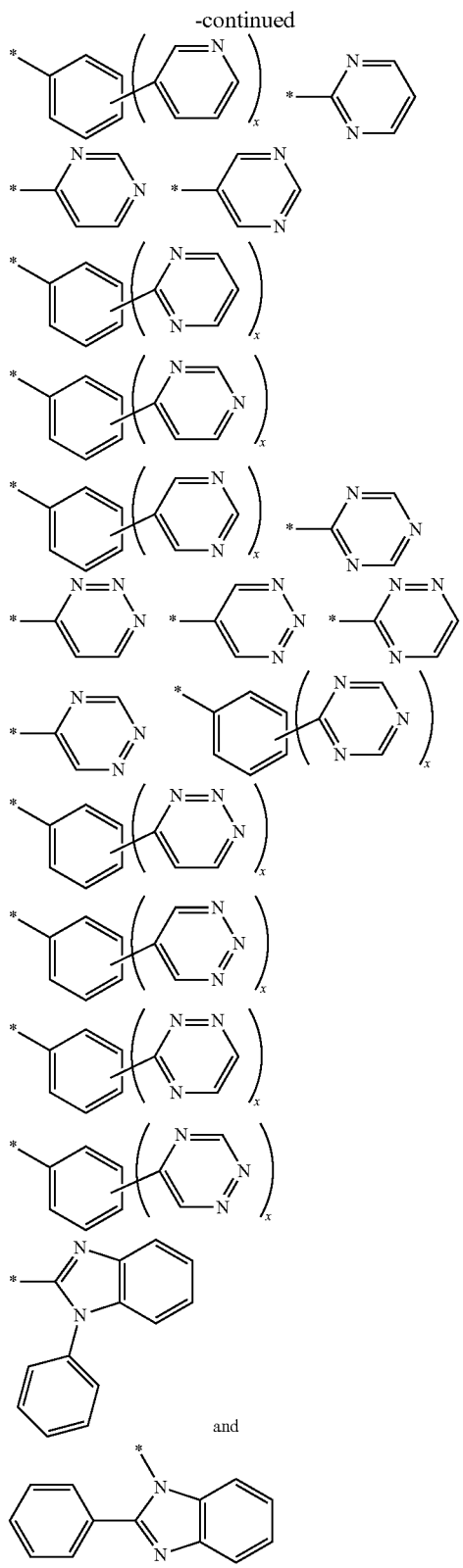

where x=1 or 2, the asterisk indicates the point of attachment to the compound, and positions available for H can be H or D.

In some embodiments of Formula I, Ar is an S-heteroaryl having at least one ring atom which is S.

In some embodiments, the S-heteroaryl or deuterated S-heteroaryl is selected from the group consisting of thiophene, (di)benzothiophene, thienothiophene, and deuterated analogs thereof. As used herein, the term "(di)benzothiophene" includes benzothiophene and dibenzothiophene.

In some embodiments, the S-heteroaryl or deuterated S-heteroaryl is selected from the group consisting of

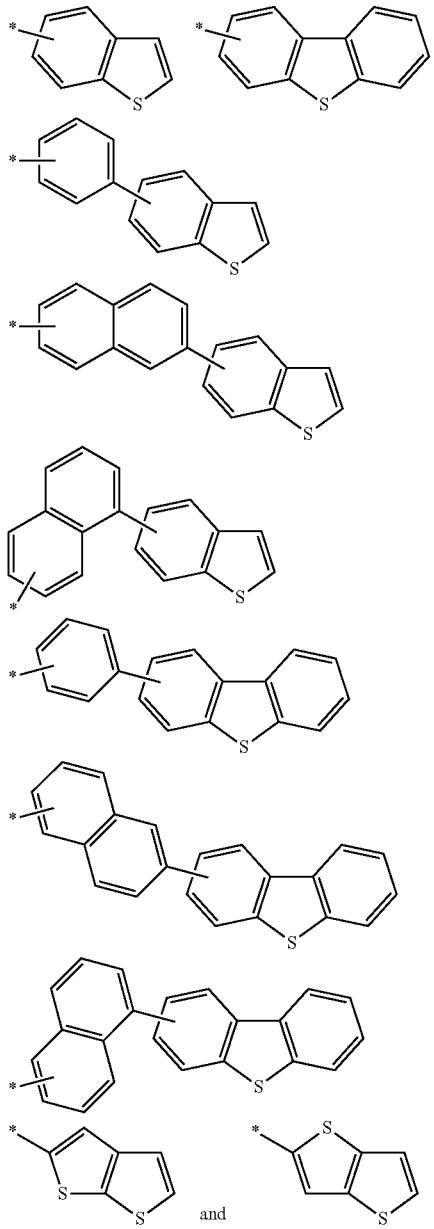

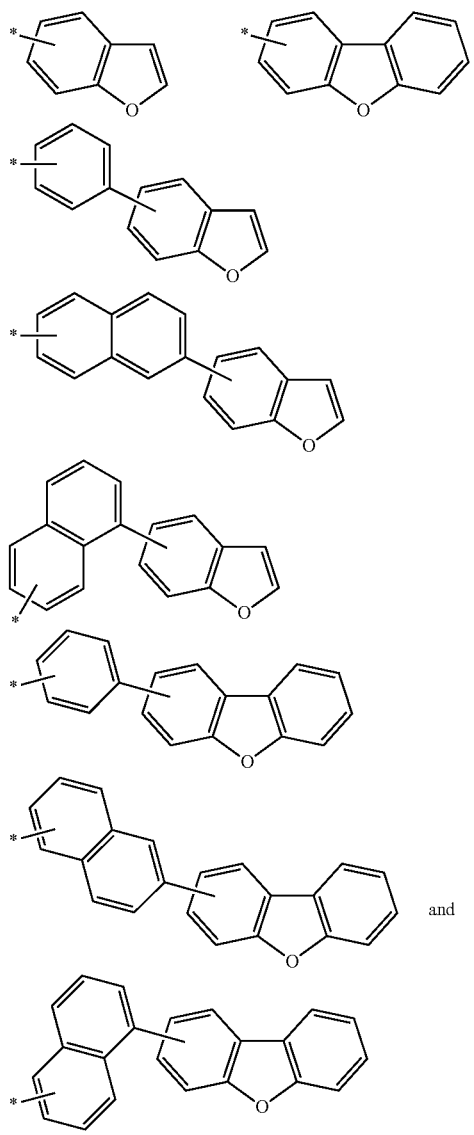

where the asterisk indicates the point of attachment to the compound, and positions available for H can be H or D.

In some embodiments of Formula I, Ar is an O-heteroaryl having at least one ring atom which is O.

In some embodiments, the O-heteroaryl or deuterated O-heteroaryl is selected from the group consisting of furan, (di)benzofuran, and deuterated analogs thereof. As used herein, the term "(di)benzofuran" includes both benzofuran and dibenzofuran.

In some embodiments, the O-heteroaryl or deuterated O-heteroaryl is selected from the group consisting of where the asterisk indicates the point of attachment to the compound, and positions available for H can be H or D.

In some embodiments of Formula I, Ar is an N,O-heteroaryl having at least one ring atom which is N and at least one ring atom which is O.

In some embodiments, the N,O-heteroaryl is selected from the group consisting of oxazole, benzoxazole, and deuterated analogs thereof.

In some embodiments of Formula I, Ar is an N,S-heteroaryl having at least one ring atom which is N and at least one ring atom that is S.

In some embodiments, the N,S-heteroaryl is selected from the group consisting of thiazole, benzothiazole, and deuterated analogs thereof.

In some embodiments of Formula I, Ar is spirofluorenyl or a deuterated analog thereof.

In some embodiments, the spirofluorenyl or deuterated spirofluorenyl moiety is selected from the group consisting of

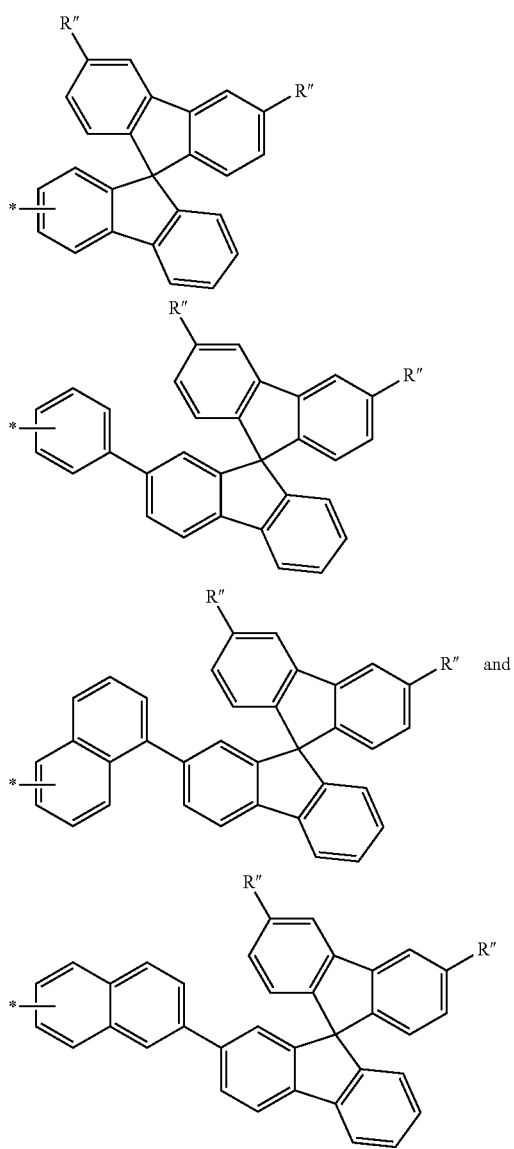
and
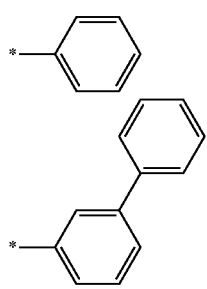
where the asterisk indicates the point of attachment to the compound, R″ is the same or different at each occurrence and is selected from the group consisting of H, D, $C_{1-12}$ alkyl, and deuterated $C_{1-12}$ alkyl, and positions available for H can be H or D.
In some embodiments of Formula I, Ar is selected from the group consisting of
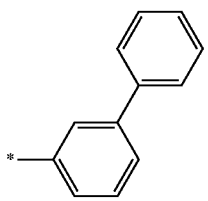
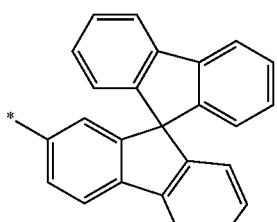
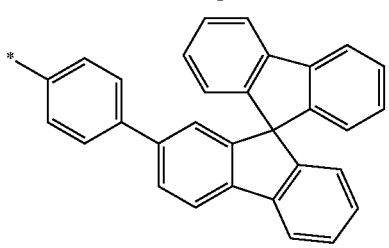
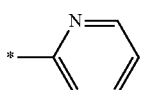
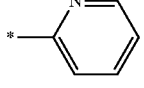
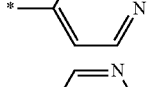
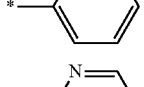
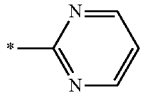
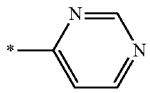
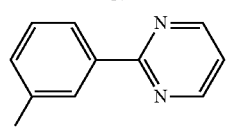
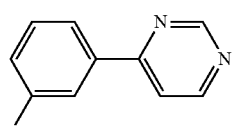
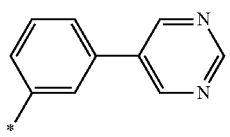

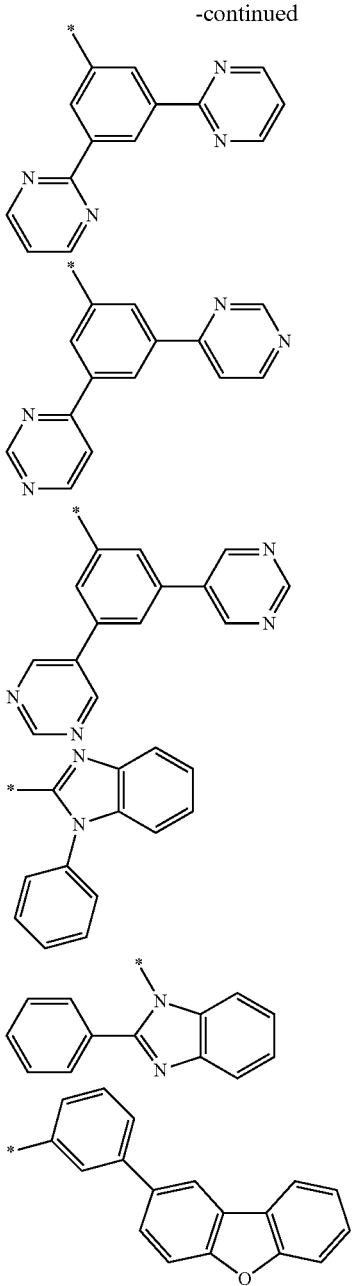

and deuterated analogs thereof, where the asterisk indicates the point of attachment to the compound.

In some embodiments of Formula I, at least one of $R^1$-$R^6$ and at least one of $R^7$-$R^{10}$ have Formula II.

In some embodiments of Formula I, at least two of $R^7$-$R^{10}$ have Formula II.

In some embodiments of Formula I, $R^1$ has Formula II.

In some embodiments of Formula I, $R^1$ is selected from the group consisting of alkyl having 1-12 carbons and deuterated analogs thereof.

In some embodiments of Formula I, $R^1$ is selected from the group consisting of silyl groups having 3-15 carbons and deuterated analogs thereof.

In some embodiments of Formula I, $R^1$ is selected from the group consisting of aryl having 6-36 ring carbons and deuterated analogs thereof.

In some embodiments of Formula I, $R^1$ is selected from the group consisting of aryl having 6-36 ring carbons having no fused rings and deuterated analogs thereof.

In some embodiments of Formula I, $R^1$ is selected from the group consisting of aryl having 6-36 ring carbons having at least one fused ring and deuterated analogs thereof.

In some embodiments of Formula I, $R^1$ is selected from the group consisting of H and D.

In some embodiments of Formula I, $R^2$ has Formula II.

In some embodiments of Formula I, $R^2$ is selected from the group consisting of alkyl having 1-12 carbons and deuterated analogs thereof.

In some embodiments of Formula I, $R^2$ is selected from the group consisting of silyl groups having 3-15 carbons and deuterated analogs thereof.

In some embodiments of Formula I, $R^2$ is selected from the group consisting of aryl having 6-36 ring carbons and deuterated analogs thereof.

In some embodiments of Formula I, $R^2$ is selected from the group consisting of aryl having 6-36 ring carbons having no fused rings and deuterated analogs thereof.

In some embodiments of Formula I, $R^2$ is selected from the group consisting of aryl having 6-36 ring carbons having at least one fused ring and deuterated analogs thereof.

In some embodiments of Formula I, $R^2$ is selected from the group consisting of H and D.

In some embodiments of Formula I, $R^3$ has Formula II.

In some embodiments of Formula I, $R^3$ is selected from the group consisting of alkyl having 1-12 carbons and deuterated analogs thereof.

In some embodiments of Formula I, $R^3$ is selected from the group consisting of silyl groups having 3-15 carbons and deuterated analogs thereof.

In some embodiments of Formula I, $R^3$ is selected from the group consisting of aryl having 6-36 ring carbons and deuterated analogs thereof.

In some embodiments of Formula I, $R^3$ is selected from the group consisting of aryl having 6-36 ring carbons having no fused rings and deuterated analogs thereof.

In some embodiments of Formula I, $R^3$ is selected from the group consisting of aryl having 6-36 ring carbons having at least one fused ring and deuterated analogs thereof.

In some embodiments of Formula I, $R^3$ is selected from the group consisting of H and D.

In some embodiments of Formula I, $R^4$ has Formula II.

In some embodiments of Formula I, $R^4$ is selected from the group consisting of alkyl having 1-12 carbons and deuterated analogs thereof.

In some embodiments of Formula I, $R^4$ is selected from the group consisting of silyl groups having 3-15 carbons and deuterated analogs thereof.

In some embodiments of Formula I, $R^4$ is selected from the group consisting of aryl having 6-36 ring carbons and deuterated analogs thereof.

In some embodiments of Formula I, $R^4$ is selected from the group consisting of aryl having 6-36 ring carbons having no fused rings and deuterated analogs thereof.

In some embodiments of Formula I, $R^4$ is selected from the group consisting of aryl having 6-36 ring carbons having at least one fused ring and deuterated analogs thereof.

In some embodiments of Formula I, $R^4$ is selected from the group consisting of H and D.

In some embodiments of Formula I, $R^5$ has Formula II.

In some embodiments of Formula I, $R^5$ is selected from the group consisting of alkyl having 1-12 carbons and deuterated analogs thereof.

In some embodiments of Formula I, $R^5$ is selected from the group consisting of silyl groups having 3-15 carbons and deuterated analogs thereof.

In some embodiments of Formula I, $R^5$ is selected from the group consisting of aryl having 6-36 ring carbons and deuterated analogs thereof.

In some embodiments of Formula I, $R^5$ is selected from the group consisting of aryl having 6-36 ring carbons having no fused rings and deuterated analogs thereof.

In some embodiments of Formula I, $R^5$ is selected from the group consisting of aryl having 6-36 ring carbons having at least one fused ring and deuterated analogs thereof.

In some embodiments of Formula I, $R^5$ is selected from the group consisting of H and D.

In some embodiments of Formula I, $R^6$ has Formula II.

In some embodiments of Formula I, $R^6$ is selected from the group consisting of alkyl having 1-12 carbons and deuterated analogs thereof.

In some embodiments of Formula I, $R^6$ is selected from the group consisting of silyl groups having 3-15 carbons and deuterated analogs thereof.

In some embodiments of Formula I, $R^6$ is selected from the group consisting of aryl having 6-36 ring carbons and deuterated analogs thereof.

In some embodiments of Formula I, $R^6$ is selected from the group consisting of aryl having 6-36 ring carbons having no fused rings and deuterated analogs thereof.

In some embodiments of Formula I, $R^6$ is selected from the group consisting of aryl having 6-36 ring carbons having at least one fused ring and deuterated analogs thereof.

In some embodiments of Formula I, $R^6$ is selected from the group consisting of H and D.

In some embodiments of Formula I, $R^7$ has Formula II.

In some embodiments of Formula I, $R^7$ is selected from the group consisting of alkyl having 1-12 carbons and deuterated analogs thereof.

In some embodiments of Formula I, $R^7$ is selected from the group consisting of silyl groups having 3-15 carbons and deuterated analogs thereof.

In some embodiments of Formula I, $R^7$ is selected from the group consisting of aryl having 6-36 ring carbons and deuterated analogs thereof.

In some embodiments of Formula I, $R^7$ is selected from the group consisting of aryl having 6-36 ring carbons having no fused rings and deuterated analogs thereof.

In some embodiments of Formula I, $R^7$ is selected from the group consisting of aryl having 6-36 ring carbons having at least one fused ring and deuterated analogs thereof.

In some embodiments of Formula I, $R^7$ is selected from the group consisting of H and D.

In some embodiments of Formula I, $R^8$ has Formula II.

In some embodiments of Formula I, $R^8$ is selected from the group consisting of alkyl having 1-12 carbons and deuterated analogs thereof.

In some embodiments of Formula I, $R^8$ is selected from the group consisting of silyl groups having 3-15 carbons and deuterated analogs thereof.

In some embodiments of Formula I, $R^8$ is selected from the group consisting of aryl having 6-36 ring carbons and deuterated analogs thereof.

In some embodiments of Formula I, $R^8$ is selected from the group consisting of aryl having 6-36 ring carbons having no fused rings and deuterated analogs thereof.

In some embodiments of Formula I, $R^8$ is selected from the group consisting of aryl having 6-36 ring carbons having at least one fused ring and deuterated analogs thereof.

In some embodiments of Formula I, $R^8$ is selected from the group consisting of H and D.

In some embodiments of Formula I, $R^9$ has Formula II.

In some embodiments of Formula I, $R^9$ is selected from the group consisting of alkyl having 1-12 carbons and deuterated analogs thereof.

In some embodiments of Formula I, $R^9$ is selected from the group consisting of silyl groups having 3-15 carbons and deuterated analogs thereof.

In some embodiments of Formula I, $R^9$ is selected from the group consisting of aryl having 6-36 ring carbons and deuterated analogs thereof.

In some embodiments of Formula I, $R^9$ is selected from the group consisting of aryl having 6-36 ring carbons having no fused rings and deuterated analogs thereof.

In some embodiments of Formula I, $R^9$ is selected from the group consisting of aryl having 6-36 ring carbons having at least one fused ring and deuterated analogs thereof.

In some embodiments of Formula I, $R^9$ is selected from the group consisting of H and D.

In some embodiments of Formula I, $R^{10}$ has Formula II.

In some embodiments of Formula I, $R^{10}$ is selected from the group consisting of alkyl having 1-12 carbons and deuterated analogs thereof.

In some embodiments of Formula I, $R^{10}$ is selected from the group consisting of silyl groups having 3-15 carbons and deuterated analogs thereof.

In some embodiments of Formula I, $R^{10}$ is selected from the group consisting of aryl having 6-36 ring carbons and deuterated analogs thereof.

In some embodiments of Formula I, $R^{10}$ is selected from the group consisting of aryl having 6-36 ring carbons having no fused rings and deuterated analogs thereof.

In some embodiments of Formula I, $R^{10}$ is selected from the group consisting of aryl having 6-36 ring carbons having at least one fused ring and deuterated analogs thereof.

In some embodiments of Formula I, $R^{10}$ is selected from the group consisting of H and D.

In some embodiments of Formula I, $m>0$ and $R^{11}$ is selected from the group consisting of alkyl having 1-12 carbons and deuterated analogs thereof.

In some embodiments of Formula I, $m>0$ and $R^{11}$ is selected from the group consisting of silyl groups having 3-15 carbons and deuterated analogs thereof.

In some embodiments of Formula I, $m>0$ and $R^{11}$ is selected from the group consisting of aryl having 6-36 ring carbons and deuterated analogs thereof.

In some embodiments of Formula I, $m>0$ and $R^{11}$ is selected from the group consisting of aryl having 6-36 ring carbons having no fused rings and deuterated analogs thereof.

In some embodiments of Formula I, $m>0$ and $R^{11}$ is selected from the group consisting of aryl having 6-36 ring carbons having at least one fused ring and deuterated analogs thereof.

In some embodiments of Formula I, $m>0$ and $R^{11}$ is D.

Any of the above specific and/or general embodiments of Formula I can be combined with one or more of the other embodiments, so long as they are not mutually exclusive. For example, the embodiments in which $R^3$ is Ar can be combined with the embodiments in which Ar is an N-heteroaryl and with the embodiments in which $R^5$ is a silyl or deuterated silyl. The embodiment in which $R^3$ is selected from the group consisting of aryl having 6-36 ring carbons and deuterated analogs thereof can be combined with the embodiment in which $R^6$ is selected from the group consisting of alkyl having 1-12 carbons and deuterated analogs thereof and with the embodiment in which $R^9$ is selected from the group consisting of H and D. The same is true for the other non-mutually-exclusive embodiments discussed above. The skilled person would understand which embodiments were mutually exclusive and would thus readily be able to determine the combinations of embodiments that are contemplated by the present application.

In some embodiments, the fluoranthene compound has Formula III

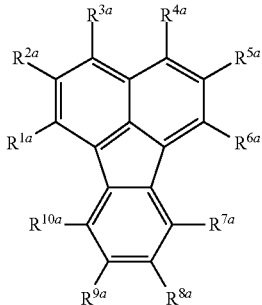

Formula III wherein:

$R^{1a}$-$R^{10a}$ are the same or different and are selected from the group consisting of H, D, alkyl, silyl, aryl, deuterated alkyl, deuterated silyl, and deuterated aryl;

with the proviso that at least one of $R^{1a}$-$R^{10a}$ includes a spirofluorene group or deuterated analog thereof.

In some embodiments of Formula III, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In Formula III, at least one of $R^{1a}$-$R^{10a}$ includes a spirofluorene group or deuterated analog thereof. By this it is meant that the spirofluorene can be attached directly to the fluoranthene core or attached to another group which is attached to the fluoranthene core.

In some embodiments of Formula III, the spirofluorenyl or deuterated spirofluorenyl moiety is selected from the group consisting of

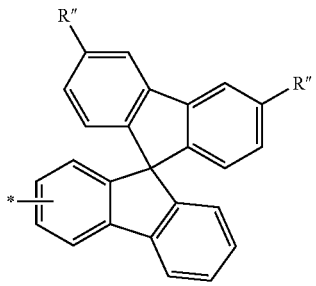

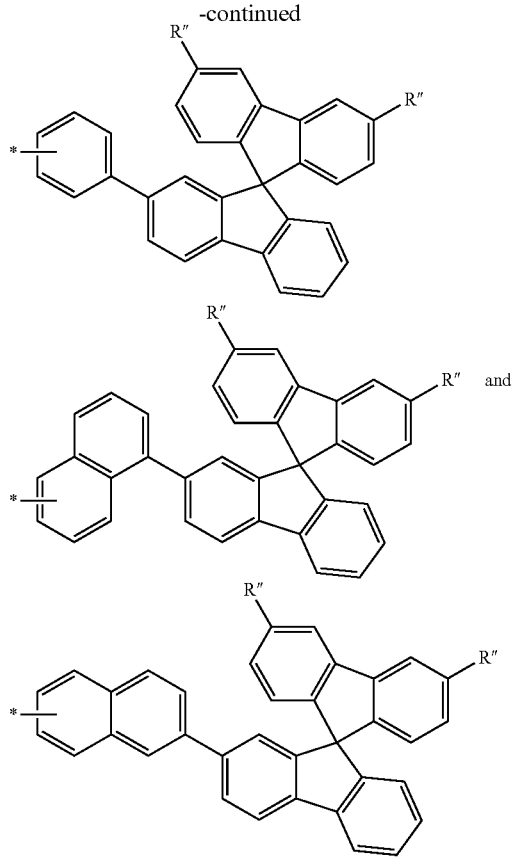

where the asterisk indicates the point of attachment to the compound, R" is the same or different at each occurrence and is selected from the group consisting of H, D, $C_{1-12}$ alkyl, and deuterated $C_{1-12}$ alkyl, and positions available for H can be H or D.

In some embodiments of Formula III, no more than one of $R^{1a}$-$R^{10a}$ is biphenyl.

In some embodiments of Formula III, none of $R^{1a}$-$R^{10a}$ is biphenyl.

In some embodiments of Formula III, at least one of $R^{1a}$-$R^{10a}$ has Formula II, as defined above, where Ar is as defined above.

In some embodiments of Formula III, $R^{1a}$ is as described above for $R^1$ of Formula I.

In some embodiments of Formula III, $R^{2a}$ is as described above for $R^2$ of Formula I.

In some embodiments of Formula III, $R^{3a}$ is as described above for $R^3$ of Formula I.

In some embodiments of Formula III, $R^{4a}$ is as described above for $R^4$ of Formula I.

In some embodiments of Formula III, $R^{5a}$ is as described above for $R^5$ of Formula I.

In some embodiments of Formula III, $R^{6a}$ is as described above for $R^6$ of Formula I.

In some embodiments of Formula III, $R^{7a}$ is as described above for $R^7$ of Formula I.

In some embodiments of Formula III, $R^{8a}$ is as described above for $R^8$ of Formula I.

In some embodiments of Formula III, $R^{9a}$ is as described above for $R^9$ of Formula I.

In some embodiments of Formula III, $R^{10a}$ is as described above for $R^{10}$ of Formula I.

Any of the above specific and/or general embodiments of Formula III can be combined with one or more of the other embodiments, so long as they are not mutually exclusive. For example, the embodiment in which $R^{3a}$ is selected from the group consisting of aryl having 6-36 ring carbons and deuterated analogs thereof can be combined with the embodiment in which $R^{6a}$ is selected from the group consisting of alkyl having 1-12 carbons and deuterated analogs thereof and with the embodiment in which $R^{9a}$ is selected from the group consisting of H and D. The same is true for the other non-mutually-exclusive embodiments discussed above. The skilled person would understand which embodiments were mutually exclusive and would thus readily be able to determine the combinations of embodiments that are contemplated by the present application.

Some examples of compounds having Formula I or Formula III are shown below.

Compound E1

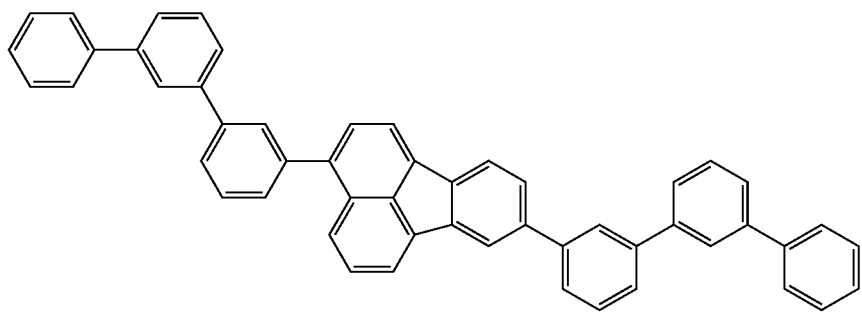

Compound E2

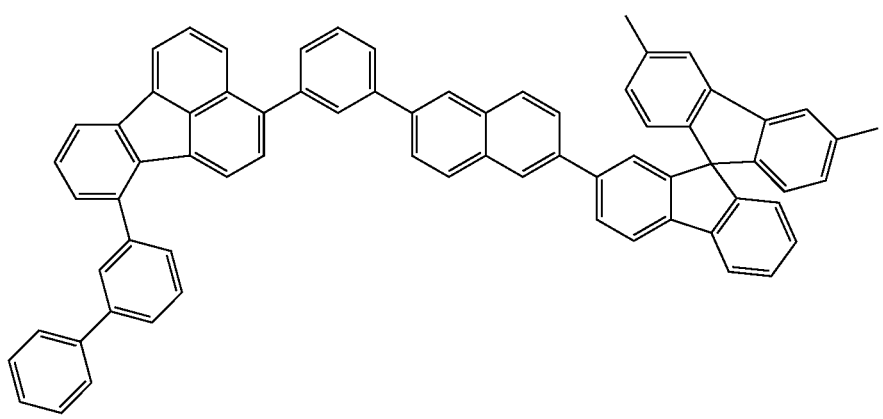

Compound E3

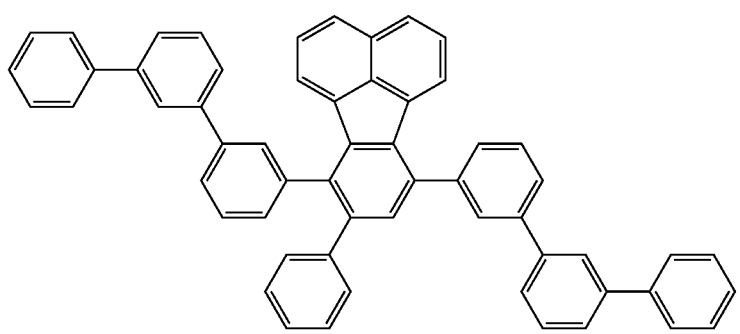

Compound E4

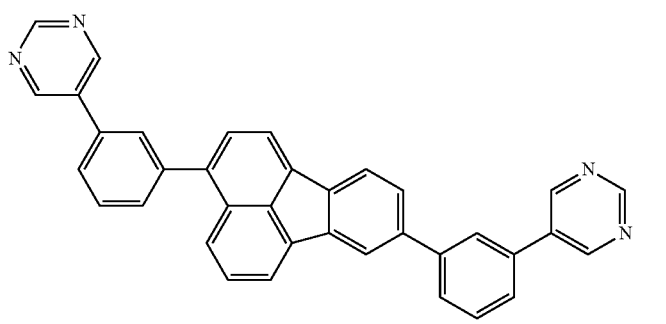

Compound E5
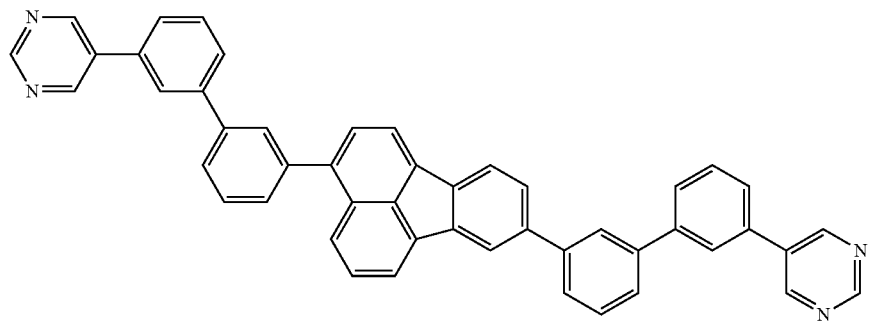
Compound E6
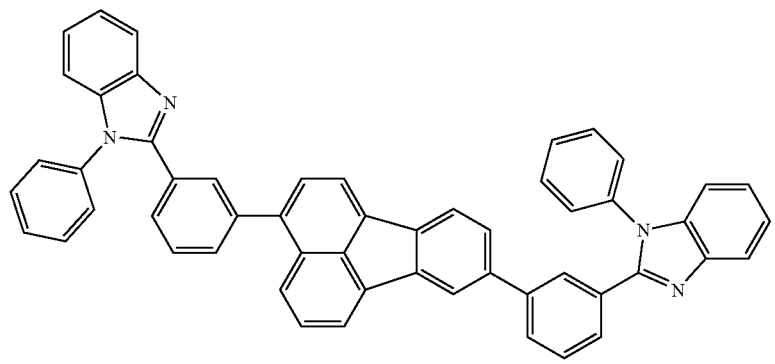
Compound E7
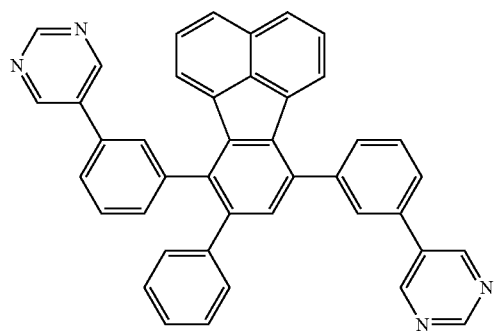
Compound E8
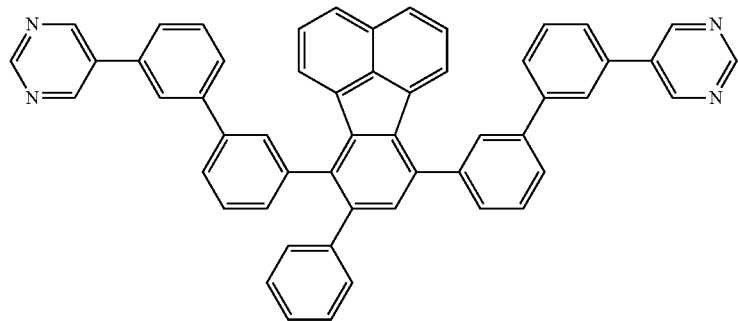

Compound E9
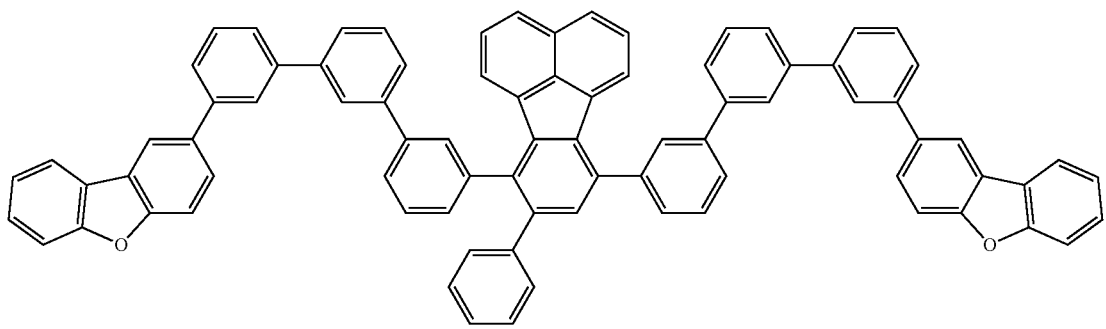
Compound E10
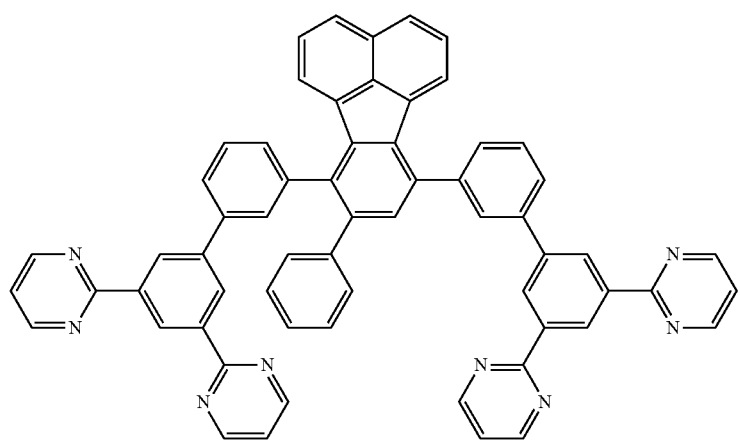
Compound E11
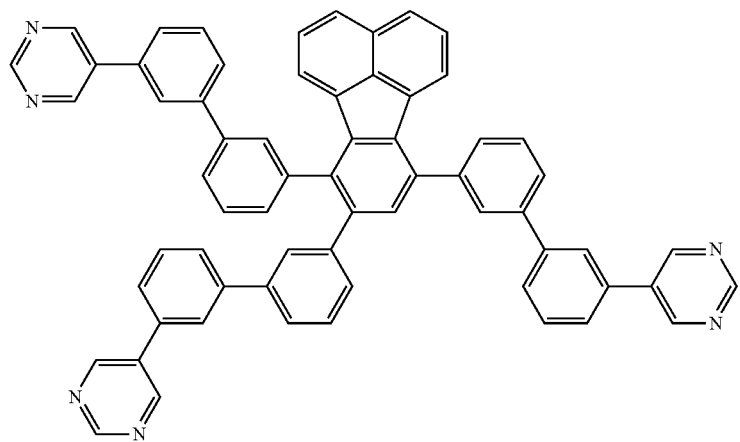

-continued
Compound E12
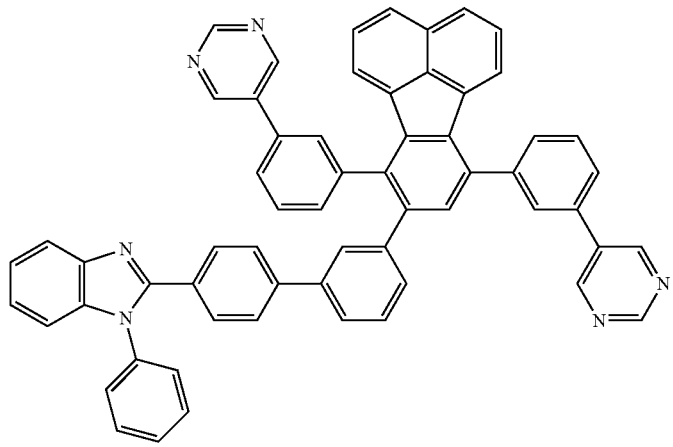
Compound E13
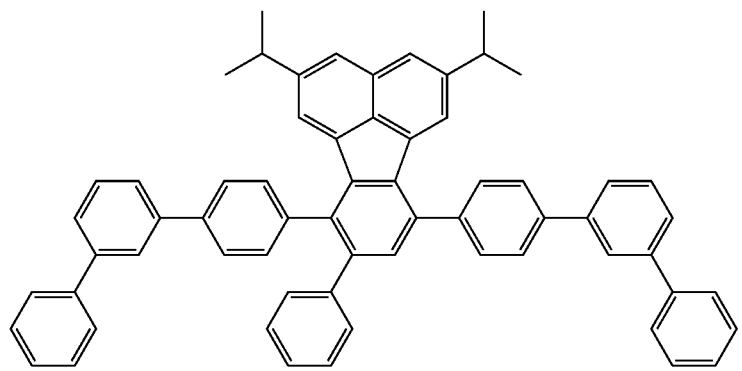
Compound E14
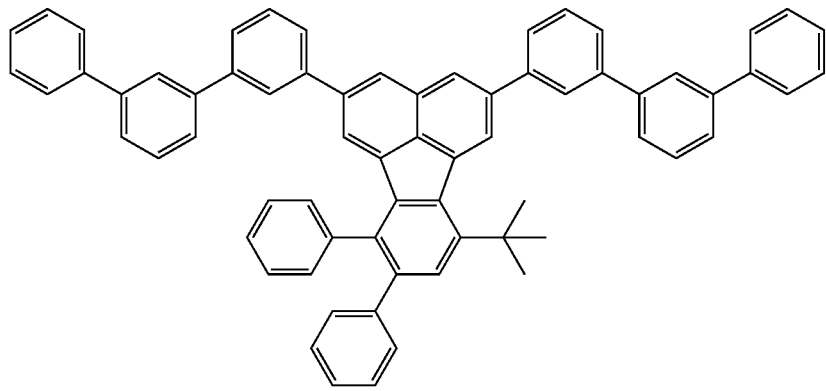
Compound E15
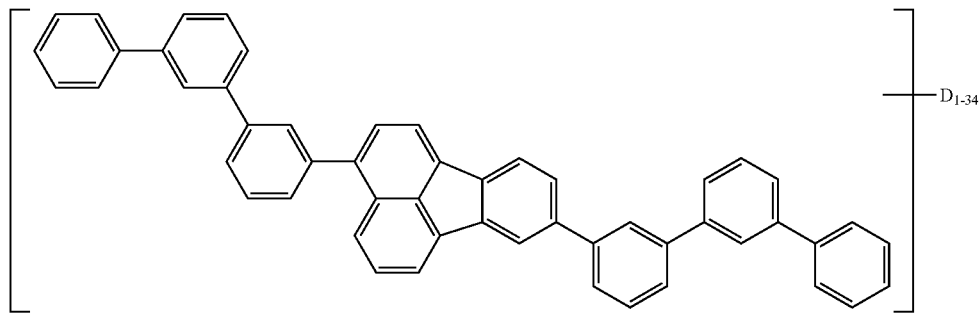

-continued
Compound E16
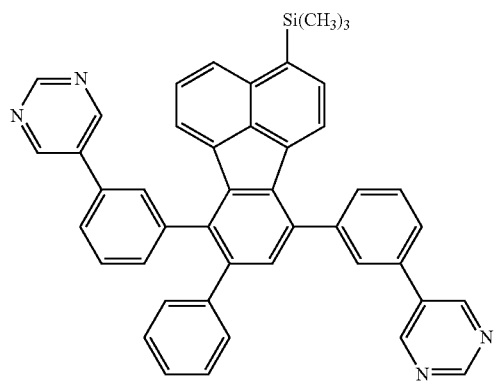
Compound E17
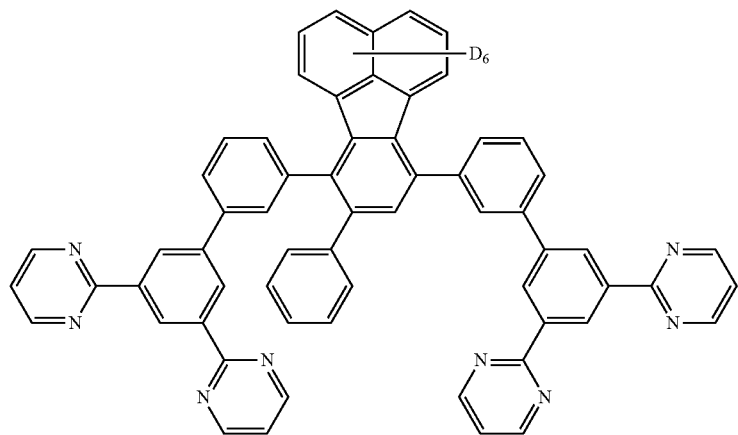
Compound E18
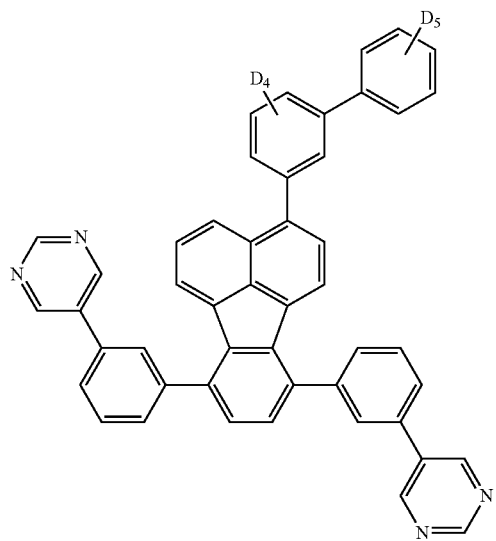

-continued
Compound E19
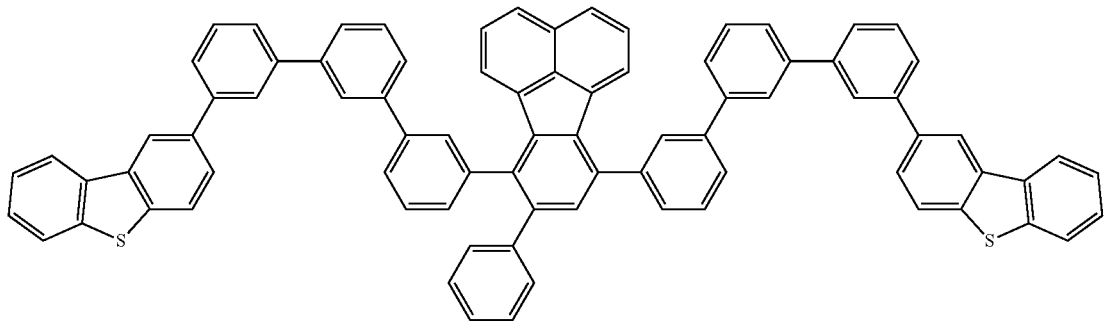
Compound E20
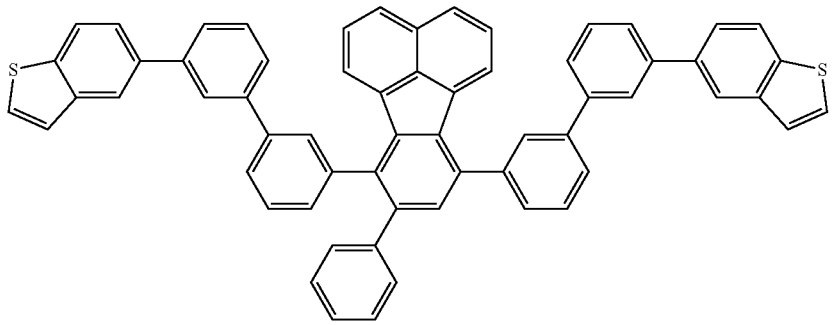
Compound E21
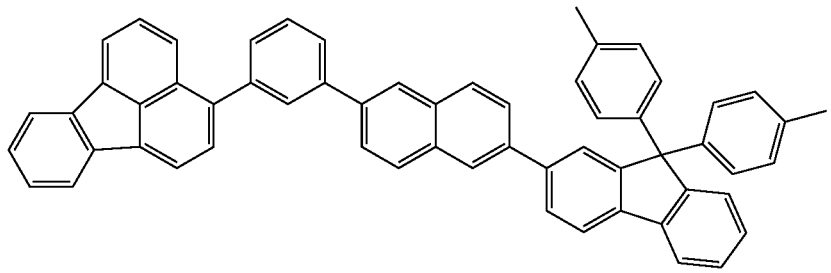
Compound E22
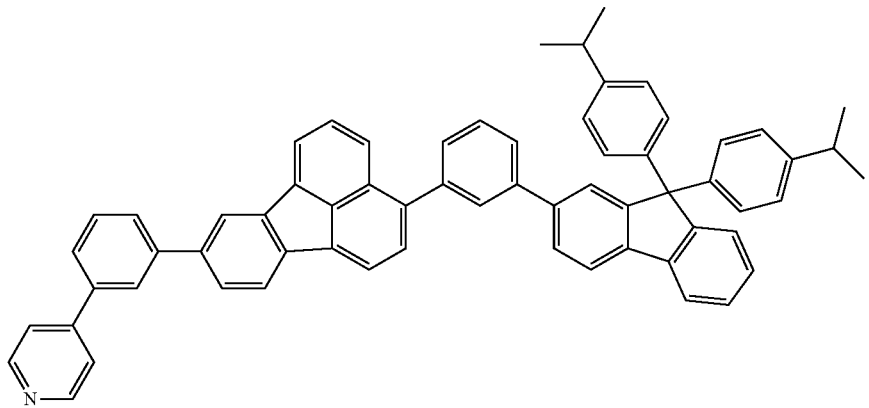
Compound E23
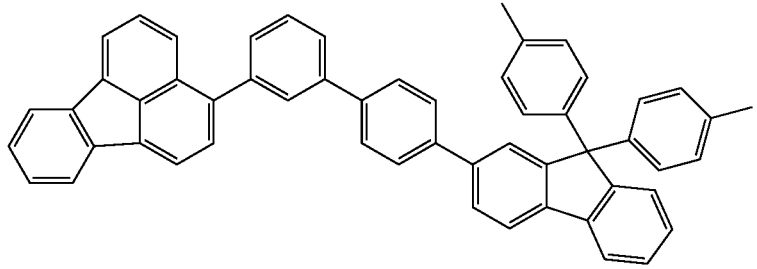

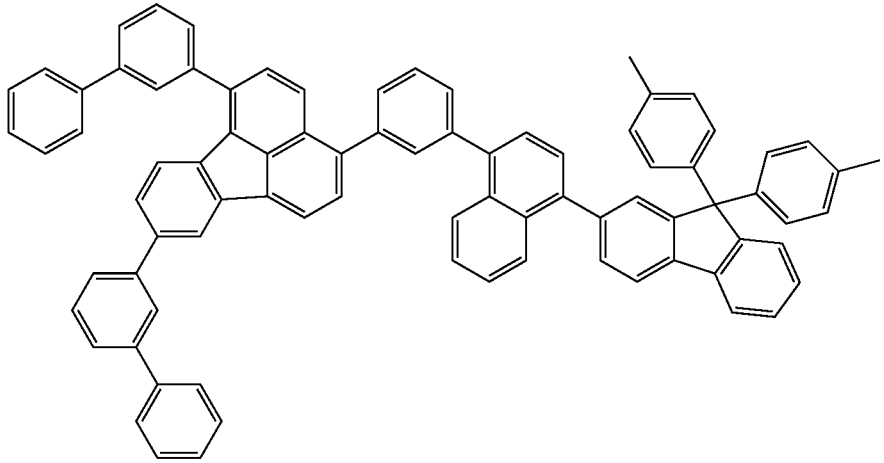

Compound E24

The fluoranthene compounds having Formula I or Formula III can be made by any technique that will yield a C—C or C—N bond. A variety of such techniques are known, such as Suzuki, Yamamoto, Stille, and Pd- or Ni-catalyzed C—N couplings.

The deuterated analog compounds can be prepared in a similar manner using deuterated precursor materials or, more generally, by treating the non-deuterated compound with deuterated solvent, such as d6-benzene, in the presence of a Lewis acid H/D exchange catalyst, such as aluminum trichloride or ethyl aluminum chloride, or acids such as $CF_3COOD$, DCI, etc. Deuteration reactions have also been described in published PCT application WO2011/053334.

Exemplary preparations are given in the Examples.

3. Electroactive Composition

There is also provided a composition including (a) a host compound having Formula I or Formula III and (b) a dopant capable of electroluminescence having an emission maximum between 380 and 750 nm. The fluoranthene derivatives of Formula I are useful as host materials for photoactive materials. The compounds can be used alone, or in combination with another host material. The compounds of Formula I can be used as a host for dopants with any color of emission. In some embodiments, the compound as used as hosts for organometallic electroluminescent material.

In some embodiments, the composition includes (a) a host compound having Formula I or Formula III and (b) a photoactive dopant capable of electroluminescence having an emission maximum between 380 and 750 nm. In some embodiments, the composition includes only (a) a host compound having Formula I or Formula III and (b) a photoactive dopant capable of electroluminescence having an emission maximum between 380 and 750 nm, where components that would materially alter the principle of operation or the distinguishing characteristics of the composition are not present.

In some embodiments, the composition includes (a) a host compound having Formula I or Formula III, (b) a photoactive dopant capable of electroluminescence having an emission maximum between 380 and 750 nm, and (c) a second host material. In some embodiments, the composition includes only (a) a host compound having Formula I or Formula III, (b) a photoactive dopant capable of electroluminescence having an emission maximum between 380 and 750 nm, and (c) a second host material, where components that would materially alter the principle of operation or the distinguishing characteristics of the composition are not present.

The amount of dopant present in the composition is generally in the range of 3-20% by weight, based on the total weight of the composition; in some embodiments, 5-15% by weight. When a second host is present, the ratio of first host having Formula I or Formula III to second host is generally in the range of 1:20 to 20:1; in some embodiments, 5:15 to 15:5. In some embodiments, the first host material having Formula I or Formula III is at least 50% by weight of the total host material; in some embodiments, at least 70% by weight.

Electroluminescent ("EL") materials which can be used as a dopant include, but are not limited to, small molecule organic luminescent compounds, luminescent metal complexes, conjugated polymers, and mixtures thereof. Examples of small molecule luminescent organic compounds include, but are not limited to, chrysenes, pyrenes, perylenes, rubrenes, coumarins, anthracenes, thiadiazoles, benzofluorenes, derivatives thereof, and mixtures thereof. Examples of metal complexes include, but are not limited to, metal chelated oxinoid compounds and cyclometallated complexes of metals such as iridium and platinum. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

Examples of green light-emitting materials include, but are not limited to, complexes of Ir having phenylpyridine ligands, bis(diarylamino)anthracenes, and polyphenylenevinylene polymers. Green light-emitting materials have been disclosed in, for example, published PCT application WO 2007/021117.

Examples of blue light-emitting materials include, but are not limited to, complexes of Ir having phenylpyridine or phenylimidazole ligands, diarylanthracenes, diaminochrysenes, diaminopyrenes, diaminobenzofluorenes, and polyfluorene polymers. Blue light-emitting materials have been disclosed in, for example, U.S. Pat. No. 6,875,524, and published US applications 2007-0292713 and 2007-0063638.

In some embodiments, the dopant is an organometallic complex. In some embodiments, the organometallic complex is cyclometallated. By "cyclometallated" it is meant that the complex contains at least one ligand which bonds to the metal in at least two points, forming at least one 5- or 6-membered ring with at least one carbon-metal bond. In some embodiments, the metal is iridium or platinum. In some embodiments, the organometallic complex is electrically neutral and is a tris-cyclometallated complex of iridium having the formula IrL$_3$ or a bis-cyclometallated complex of iridium having the formula IrL$_2$Y. In some embodiments, L is a monoanionic bidentate cyclometalating ligand coordinated through a carbon atom and a nitrogen atom. In some embodiments, L is an aryl N-heterocycle, where the aryl is phenyl or napthyl, and the N-heterocycle is pyridine, quinoline, isoquinoline, diazine, pyrrole, pyrazole or imidazole. In some embodiments, Y is a monoanionic bidentate ligand. In some embodiments, L is a phenylpyridine, a phenylquinoline, or a phenylisoquinoline. In some embodiments, Y is a β-dienolate, a diketimine, a picolinate, or an N-alkoxypyrazole. The ligands may be unsubstituted or substituted with F, D, alkyl, perfluororalkyl, alkoxyl, alkylamino, arylamino, CN, silyl, fluoroalkoxyl or aryl groups.

In some embodiments, the dopant is a cyclometalated complex of iridium or platinum. Such materials have been disclosed in, for example, U.S. Pat. No. 6,670,645 and Published PCT Applications WO 03/063555, WO 2004/016710, and WO 03/040257.

In some embodiments, the dopant is a complex having the formula Ir(L1)$_a$(L2)$_b$ (L3)$_c$; where
  L1 is a monoanionic bidentate cyclometalating ligand coordinated through carbon and nitrogen;
  L2 is a monoanionic bidentate ligand which is not coordinated through a carbon;
  L3 is a monodentate ligand;
  a is 1-3;
  b and c are independently 0-2; and
  a, b, and c are selected such that the iridium is hexacoordinate and the complex is electrically neutral.
Some examples of formulae include, but are not limited to, Ir(L1)$_3$; Ir(L1)$_2$(L2); and Ir(L1)$_2$(L3)(L3'), where L3 is anionic and L3' is nonionic.

Examples of L1 ligands include, but are not limited to phenylpyridines, phenylquinolines, phenylpyrimidines, phenylpyrazoles, thienylpyridines, thienylquinolines, and thienylpyrimidines. As used herein, the term "quinolines" includes "isoquinolines" unless otherwise specified. The fluorinated derivatives can have one or more fluorine substituents. In some embodiments, there are 1-3 fluorine substituents on the non-nitrogen ring of the ligand.

Monoanionic bidentate ligands, L2, are well known in the art of metal coordination chemistry. In general these ligands have N, O, P, or S as coordinating atoms and form 5- or 6-membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids (aminocarboxylate ligands); pyridine carboxylic acids (iminocarboxylate ligands); salicylic acid derivatives (salicylate ligands); hydroxyquinolines (hydroxyquinolinate ligands) and their S analogs; and phosphinoalkanols (phosphinoalkoxide ligands).

Monodentate ligand L3 can be anionic or nonionic. Anionic ligands include, but are not limited to, H$^-$ ("hydride") and ligands having C, O or S as coordinating atoms. Coordinating groups include, but are not limited to alkoxide, carboxylate, thiocarboxylate, dithiocarboxylate, sulfonate, thiolate, carbamate, dithiocarbamate, thiocarbazone anions, sulfonamide anions, and the like. In some cases, ligands listed above as L2, such as β-enolates and phosphinoakoxides, can act as monodentate ligands. The monodentate ligand can also be a coordinating anion such as halide, cyanide, isocyanide, nitrate, sulfate, hexahaloantimonate, and the like. These ligands are generally available commercially.

The monodentate L3 ligand can also be a non-ionic ligand, such as CO or a monodentate phosphine ligand.

In some embodiments, one or more of the ligands has at least one substituent selected from the group consisting of F and fluorinated alkyls. The iridium complex dopants can be made using standard synthetic techniques as described in, for example, U.S. Pat. No. 6,670,645.

In some embodiments, the dopant is a small organic luminescent compound. In some embodiments, the dopant is selected from the group consisting of a non-polymeric spirobifluorene compound and a fluoranthene compound.

In some embodiments, the dopant is a compound having aryl amine groups. In some embodiments, the photoactive dopant is selected from the formulae below:

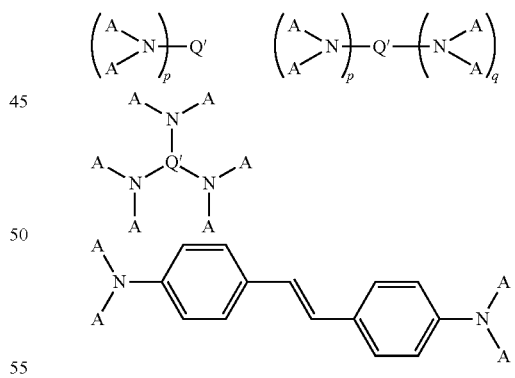

where:
  A is the same or different at each occurrence and is an aromatic group having from 3-60 carbon atoms;
  Q' is a single bond or an aromatic group having from 3-60 carbon atoms;
  p and q are independently an integer from 1-6.
In some embodiments of the above formula, at least one of A and Q' in each formula has at least three condensed rings. In some embodiments, p and q are equal to 1.

In some embodiments, Q' is a styryl or styrylphenyl group.

In some embodiments, Q' is an aromatic group having at least two condensed rings. In some embodiments, Q' is selected from the group consisting of naphthalene, anthracene, chrysene, pyrene, tetracene, xanthene, perylene, coumarin, rhodamine, quinacridone, and rubrene.

In some embodiments, A is selected from the group consisting of phenyl, biphenyl, tolyl, naphthyl, naphthylphenyl, and anthracenyl groups.

In some embodiments, the dopant has the formula below:

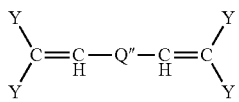

where:

Y is the same or different at each occurrence and is an aromatic group having 3-60 carbon atoms;

Q'' is an aromatic group, a divalent triphenylamine residue group, or a single bond.

In some embodiments, the dopant is an aryl acene. In some embodiments, the dopant is a non-symmetrical aryl acene.

In some embodiments, the photoactive dopant is a chrysene derivative. The term "chrysene" is intended to mean 1,2-benzophenanthrene. In some embodiments, the photoactive dopant is a chrysene having aryl substituents. In some embodiments, the photoactive dopant is a chrysene having arylamino substituents. In some embodiments, the photoactive dopant is a chrysene having two different arylamino substituents. In some embodiments, the chrysene derivative has a deep blue emission.

In some embodiments, the fluoranthene derivative compound is used with an additional host material. In some embodiments, the fluoranthene derivative compound is not used as a host in the photoactive layer. Examples of other types of hosts which can be used alone or in combination with the fluoranthene derivative compounds, include, but are not limited to, indolocarbazoles, chrysenes, phenanthrenes, triphenylenes, phenanthrolines, triazines, naphthalenes, anthracenes, quinolines, isoquinolines, quinoxalines, phenylpyridines, benzodifurans, and metal quinolinate complexes, and deuterated analogs thereof.

4. Organic Electronic Device

Organic electronic devices that may benefit from having one or more layers including the materials described herein include, but are not limited to, (1) devices that convert electrical energy into radiation (e.g., a light-emitting diode, light-emitting diode display, light-emitting luminaire, or diode laser), (2) devices that detect signals through electronics processes (e.g., photodetectors, photoconductive cells, photoresistors, photoswitches, phototransistors, phototubes, IR detectors), (3) devices that convert radiation into electrical energy, (e.g., a photovoltaic device or solar cell), and (4) devices that include one or more electronic components that include one or more organic semi-conductor layers (e.g., a thin film transistor or diode). The compounds described herein often can be useful in applications such as oxygen sensitive indicators and as luminescent indicators in bioassays.

In some embodiments, an organic electronic device includes at least one layer including the compound having Formula I or Formula III as discussed above.

In some embodiments, an electronic device includes at least one electroactive layer positioned between two electrical contact layers, wherein the at least one electroactive layer of the device includes a fluoranthene derivative compound having Formula I or Formula III.

An example of an organic electronic device structure is shown in FIG. 1. The device 200 has a first electrical contact layer, an anode layer 210 and a second electrical contact layer, a cathode layer 260, and a photoactive layer 240 between them. Adjacent to the anode may be a hole injection layer 220. Adjacent to the hole injection layer may be a hole transport layer 230, including hole transport material. Adjacent to the cathode may be an electron transport layer 250, including an electron transport material. Devices may use one or more additional hole injection or hole transport layers (not shown) next to the anode 210 and/or one or more additional electron injection or electron transport layers (not shown) next to the cathode 260.

Layers 220 through 250 are individually and collectively referred to as the electroactive layers.

Figure 2:
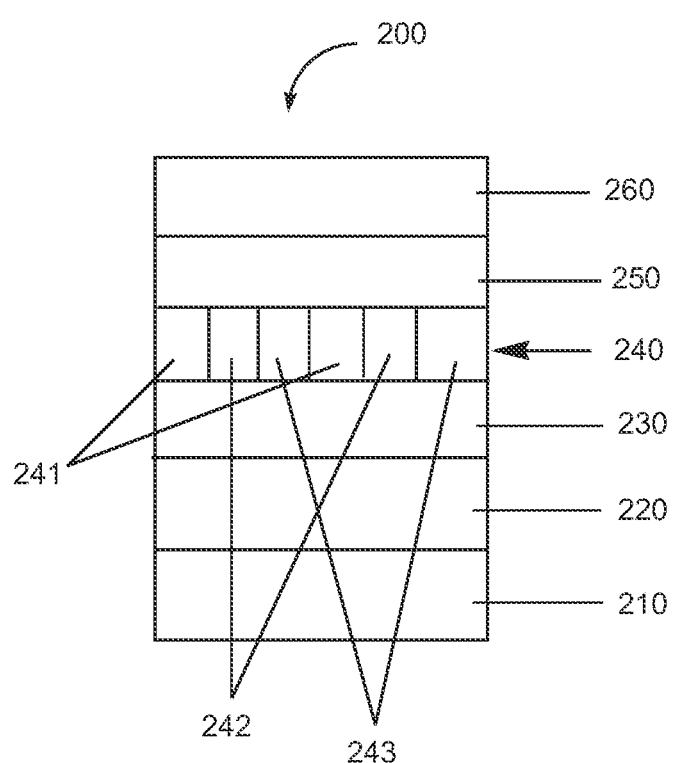
FIG. 2 includes a schematic diagram of another example of an organic electronic device.

In some embodiments, the photoactive layer 240 is pixilated, as shown in FIG. 2. Layer 240 is divided into pixel or subpixel units 241, 242, and 243 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 210, 500-5000 Å, in some embodiments 1000-2000 Å; hole injection layer 220, 50-2000 Å, in some embodiments 200-1000 Å; hole transport layer 230, 50-3000 Å, in some embodiments, 50-2000 Å, in some embodiments, 200-2000 Å, in some embodiments 200-1000 Å; electroactive layer 240, 10-2000 Å, in some embodiments 100-1000 Å; layer 250, 50-2000 Å, in some embodiments 100-1000 Å; cathode 260, 200-10000 Å, in some embodiments 300-5000 Å. The location of the electron-hole recombination zone in the device, and thus the emission spectrum of the device, can be affected by the relative thickness of each layer. The desired ratio of layer thicknesses will depend on the exact nature of the materials used. In some embodiments, the devices have additional layers to aid in processing or to improve functionality.

Depending upon the application of the device 200, the photoactive layer 240 can be a light-emitting layer that is activated by an applied voltage (such as in a light-emitting diode or light-emitting electrochemical cell), or a layer of material that responds to radiant energy and generates a signal with or without an applied bias voltage (such as in a photodetector). Examples of photodetectors include photoconductive cells, photoresistors, photoswitches, phototransistors, and phototubes, and photovoltaic cells, as these terms are described in Markus, John, *Electronics and Nucleonics Dictionary*, 470 and 476 (McGraw-Hill, Inc. 1966). Devices with light-emitting layers may be used to form displays or for lighting applications, such as white light luminaires.

One or more of the new electroactive compounds described herein may be present in one or more of the electroactive layers of a device.

In some embodiments, the new electroactive compounds having Formula I or Formula III are useful as host materials for photoactive dopant materials in photoactive layer 240. It has been found that when these compounds are used by themselves or in conjunction with other cohosts, they can provide improved efficiency and lifetime in OLED devices. It has been discovered through calculations that these compounds have high triplet energies and HOMO and LUMO levels appropriate for charge transport, making them excellent host materials for organometallic emitters.

In some embodiments, the new electroactive compounds are useful as electron transport materials in layer 250.

Photoactive Layer

In some embodiments, the photoactive layer 240 includes the electroactive composition described above.

In some embodiments, the dopant is an organometallic material. In some embodiments, the organometallic material is a complex of Ir or Pt.

In some embodiments, the organometallic material is a cyclometallated complex of Ir.

In some embodiments, the photoactive layer includes (a) a host material having Formula I or Formula III and (b) one or more dopants. In some embodiments, the photoactive layer includes (a) a host material having Formula I or Formula III and (b) an organometallic electroluminescent dopant. In some embodiments, the photoactive layer includes (a) a host material having Formula I or Formula III, (b) a photoactive dopant, and (c) a second host material. In some embodiments, the photoactive layer includes (a) a host material having Formula I or Formula III, (b) an organometallic complex of Ir or Pt, and (c) a second host material. In some embodiments, the photoactive layer includes (a) a host material having Formula I or Formula III, (b) a cyclometallated complex of Ir, and (c) a second host material.

In some embodiments, the photoactive layer includes only (a) a host material having Formula I or Formula III and (b) one or more dopants, where components that would materially alter the principle of operation or the distinguishing characteristics of the composition are not present. In some embodiments, the photoactive layer includes only (a) a host material having Formula I or Formula III and (b) an organometallic electroluminescent dopant. In some embodiments, the photoactive layer includes only (a) a host material having Formula I or Formula III, (b) a photoactive dopant, and (c) a second host material. In some embodiments, the photoactive layer includes only (a) a host material having Formula I or Formula III, (b) an organometallic complex of Ir or Pt, and (c) a second host material. In some embodiments, the photoactive layer includes only (a) a host material having Formula I or Formula III, (b) a cyclometallated complex of Ir, and (c) a second host material.

In some embodiments, the photoactive layer includes only (a) a host material having Formula I or Formula III, wherein the compound is deuterated, and (b) one or more dopants, where components that would materially alter the principle of operation or the distinguishing characteristics of the composition are not present. In some embodiments, the photoactive layer includes only a host material having Formula I or Formula III, wherein the compound is deuterated, and (b) an organometallic electroluminescent dopant. In some embodiments, the photoactive layer includes only (a) a host material having Formula I or Formula III, wherein the compound is deuterated, (b) a photoactive dopant, and (c) a second host material. In some embodiments, the photoactive layer includes only a host material having Formula I or Formula III, wherein the compound is deuterated, (b) an organometallic complex of Ir or Pt, and (c) a second host material. In some embodiments, the photoactive layer includes only (a) a host material having Formula I or Formula III, wherein the compound is deuterated a host material having Formula I or Formula III, wherein the compound is deuterated, (b) a cyclometallated complex of Ir, and (c) a second host material. In some embodiments, the deuterated compound of Formula I is at least 10% deuterated; in some embodiments, at least 50% deuterated. In some embodiments, the second host material is deuterated. In some embodiments, the second host material is at least 10% deuterated; in some embodiments, at least 50% deuterated.

Electron Transport Layer

The fluoranthene derivative compounds of Formula I are useful as electron transport materials in layer 250. The compounds can be used alone, or in combination with another electron transport material. In some embodiments, the electron transport layer includes only a fluoranthene derivative compound having Formula I or Formula III, where components that would materially alter the principle of operation or the distinguishing characteristics of the composition are not present.

In some embodiments, other electron transport materials are used in layer 250. Examples of other electron transport materials include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri(phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport material is selected from the group consisting of metal quinolates and phenanthroline derivatives. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

Other Device Layers

The other layers in the device can be made of any materials that are known to be useful in such layers.

The anode 210 is an electrode that is particularly efficient for injecting positive charge carriers. It can be made of, for example, materials containing a metal, mixed metal, alloy, metal oxide or mixed-metal oxide, or it can be a conducting polymer, or mixtures thereof. Suitable metals include the Group 11 metals, the metals in Groups 4-6, and the Group 8-10 transition metals. If the anode is to be light-transmitting, mixed-metal oxides of Groups 12, 13 and 14 metals, such as indium-tin-oxide, are generally used. The anode 210 can also be made from an organic material such as polyaniline as described in "Flexible light-emitting diodes made from soluble conducting polymer," *Nature* vol. 357, pp 477-479 (11 Jun. 1992). At least one of the anode and cathode is desirably at least partially transparent to allow the generated light to be observed.

The hole injection layer 220 includes hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. Hole injection materials may be polymers, oligomers, or small molecules. They may be vapor deposited or deposited from liquids which may be in the form of solutions, dispersions, suspensions, emulsions, colloidal mixtures, or other compositions.

The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can include charge transfer compounds, and the like, such as copper phthalocyanine and the tetrathiafulvalene-tetracyanoquinodimethane system (TTF-TCNQ).

In some embodiments, the hole injection layer includes at least one electrically conductive polymer and at least one fluorinated acid polymer. In some embodiments, the hole injection layer includes an electrically conductive polymer doped with a fluorinated acid polymer. Such materials have been described in, for example, published U.S. patent applications US 2004/0102577, US 2004/0127637, US 2005/0205860, and published PCT application WO 2009/018009.

Examples of hole transport materials for layer 230 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), α-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl] pyrazoline (PPR or DEASP), 1,2-trans-bis(9H-carbazol-9-yl)cyclobutane (DCZB), N,N,N',N'-tetrakis(4-methyl phenyl)-(1,1'-biphenyl)-4,4'-diamine (TTB), N,N'-bis(naphthalen-1-yl)-N,N'-bis-(phenyl)benzidine (α-NPB), and porphyrinic compounds, such as copper phthalocyanine. Commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable. In some embodiments, the hole transport layer further includes a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

The cathode 260 is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used. Li- or Cs-containing organometallic compounds, LiF, CsF, and Li$_2$O can also be deposited between the organic layer and the cathode layer to lower the operating voltage.

It is known to have other layers in organic electronic devices. For example, there can be a layer (not shown) between the anode 210 and hole injection layer 220 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 210, electroactive layers 220, 230, 240, and 250, or cathode layer 260, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

The device can be prepared by a variety of techniques, including sequential vapor deposition of the individual layers on a suitable substrate. Substrates such as glass, plastics, and metals can be used. Conventional vapor deposition techniques can be used, such as thermal evaporation, chemical vapor deposition, and the like. Alternatively, the organic layers can be applied from solutions or dispersions in suitable solvents, using conventional coating or printing techniques, including but not limited to spin-coating, dip-coating, roll-to-roll techniques, ink-jet printing, screen-printing, gravure printing and the like.

In some embodiments, the device is fabricated by liquid deposition of the buffer layer, the hole transport layer, and the photoactive layer, and by vapor deposition of the anode, the electron transport layer, an electron injection layer and the cathode.

To achieve a high efficiency LED, the HOMO (highest occupied molecular orbital) of the hole transport material desirably aligns with the work function of the anode, and the LUMO (lowest un-occupied molecular orbital) of the electron transport material desirably aligns with the work function of the cathode. Chemical compatibility and sublimation temperature of the materials may also be considerations in selecting the electron and hole transport materials.

It is understood that the efficiency of devices made with the fluoranthene derivative compounds described herein, can be further improved by optimizing the other layers in the device. For example, more efficient cathodes such as Ca, Ba or LiF can be used. Shaped substrates and novel hole transport materials that result in a reduction in operating voltage or increase quantum efficiency are also applicable. Additional layers can also be added to tailor the energy levels of the various layers and facilitate electroluminescence.

EXAMPLES

The concepts described herein will be further described in the following examples, which do not limit the scope of the invention described in the claims.

Synthesis Example 1

This example illustrates the synthesis of a compound having Formula I, Compound E8.

5,5'-((8-phenylfluoranthene-7,10-diyl)bis([1,1'-biphenyl]-3',3-diyl))dipyrimidine

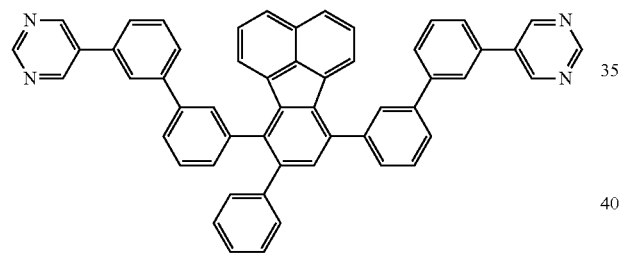

To a 250 mL round bottle flask were added 7,10-bis(3-bromophenyl)-8-phenylfluoranthene (2.94 g, 5.0 mmol), 5-(3-(4,4,5,5-tetramethyl-1,3,2-dioxaborolan-2-yl)phenyl)pyrimidine (2.96 g, 10.5 mmol), sodium carbonate (2 M, 20 mL, 40 mmol) and glyme (90 mL). The mixture was stirred under nitrogen for 20 min. Palladium acetate (56 mg, 0.25 mmol) was added and the reaction was stirred and refluxed in an oil bath at 100° C. under nitrogen for 18 hour. After cooling to ambient temperature the solid was filtered off and washed with water. The filtrate was extracted with toluene (2×50 mL). The organic layer was washed with diluted HCl (10%, 50 mL), saturated brine (50 mL), and dried with magnesium sulfate. After filtering, the solvent was evaporated and the residue was re-dissolved in DCM (30 mL). The solution was passed through an Alumina (basic) column eluted with DCM first then with DCM/iPrOH (3/1). The product containing fractions were collected and the solvent was removed by rotary evaporation. The residue was dissolved in DCM (8 mL) and the solution was added to methanol (150 mL) with stirring. The precipitate was filtered off, washed with methanol and dried in vacuum oven overnight to give the product as a light-yellow powder. Yield, 3.6 g. NMR spectra were consistent with the structure. The material was further purified by automated preparative chromatography.

Synthesis Example 2

This example illustrates the synthesis of a compound having Formula I, Compound E3.

7,10-di([1,1':3',1''-terphenyl]-3-yl)-8-phenylfluoranthene

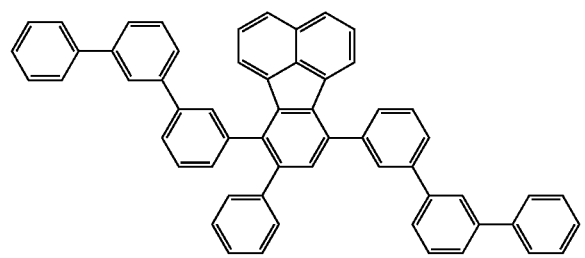 [SMILES: c1ccc(-c2cccc(-c3cccc(-c4cc(-c5ccccc5)c(-c5cccc(-c6cccc(-c7ccccc7)c6)c5)c5c4-c4cccc6cccc-5c46)c3)c2)cc1]

Step a. 7,9-bis(3-bromophenyl)-8H-cyclopenta[a]acenaphthylen-8-oneone

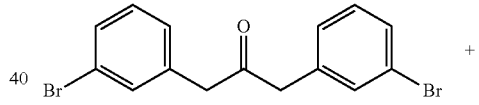

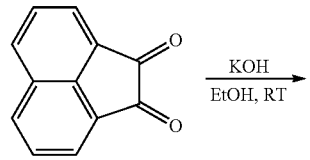

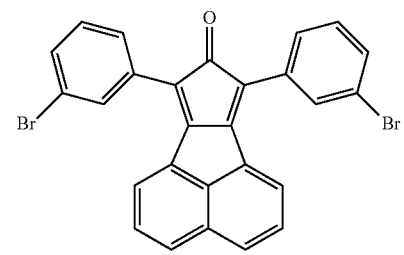

To a 250 mL three-necked RB flask equipped with a nitrogen in-line, were added 1,3-bis(3-bromophenyl)propan-2-one (4.20 g, 11.41 mmol) and acenaphthylene-1,2-dione (2.12 g, 11.63 mmol), toluene (2 mL) and ethanol (25 mL). Saturated solution of potassium hydroxide in EtOH (4.0 mL) was added dropwise to the solution in 10 min. After Step b.
7,10-bis(3-bromophenyl)-8-phenylfluoranthene Step c. 7,10-di([1,1':3',1''-terphenyl]-3-yl)-8-phenyl-fluoranthene

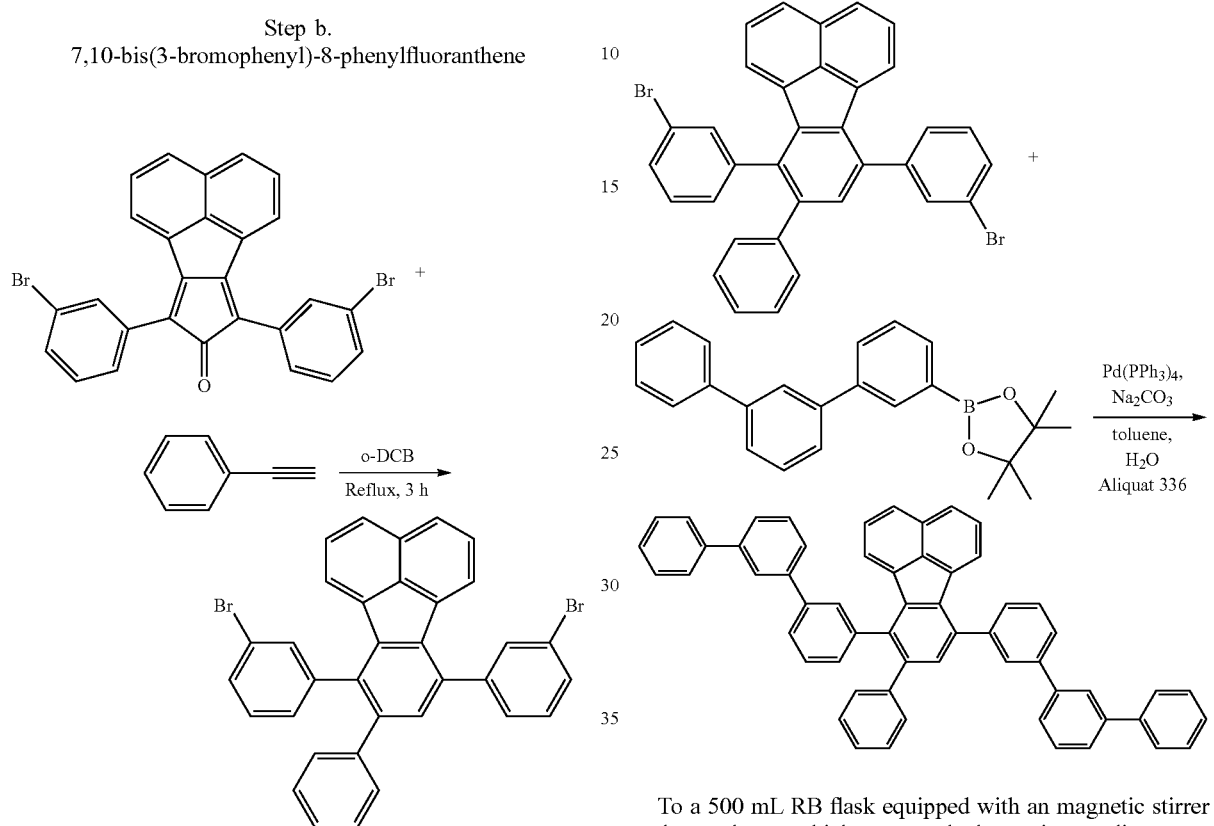

7,9-bis(3-bromophenyl)-8H-cyclopenta[a]acenaphth-ylen-8-one (4.11 g, 8.00 mmol), ethynylbenzene (1.23 g, 12.00 mmol) and 1,2-dichlorobenzene (50 mL) were added to a 3-necked RB flask. The reaction was heated to 220° C. under nitrogen for 1 hr then stirred at 180° C. overnight. UPLC analysis indicated that all 7,9-bis(3-bromophenyl)-8H-cyclopenta[a]acenaphthylen-8-one had been consumed and the product was formed as the exclusive component in the sample. The mixture was passed through a Silica gel pad eluted with toluene. The solvent was removed by rotary evaporation and the residue was separated on Silica gel column eluted with hexane first, then with hexane/DCM (1/1). The product containing fractions were combined and the solvent was removed by rotary evaporation. The residual solid, that had a tan color, was re-dissolved in DCM and refluxed with charcoal (10 g) at RT for 4 hours. The mixture was filtered and the solvent was removed by rotary evaporation. The residual solid was crystallized from DCM/acetonitrile to give the product as a light-brown crystalline material. Yield, 3.9 5 (83.8%) g in 99% purity by UPLC analysis. The structure was confirmed by NMR analysis.

To a 500 mL RB flask equipped with an magnetic stirrer and a condenser which was attached to a nitrogen line, were added 7,10-bis(3-bromophenyl)-8-phenylfluoranthene (2.65 g, 4.50 mmol), 2-(fluoranthen-3-yl)-4,4,5,5-tetramethyl-1,3,2-dioxaborolane (2.28 g, 9.18 mmol), sodium carbonate (2 M, 12 mL) and toluene (66 mL). The mixture was bubbled with nitrogen for 15 min. Tetrakis(triphenylphospine)palladium (104 mg, 0.09 mmol) was then added and the system was purged for another 15 min. The reaction mixture was stirred and refluxed in a heating block at 97° C. under nitrogen overnight. During the time the reaction solution maintained a light-brown color. After cooling down to RT, the organic phase was separated and the aqueous layer was extracted with toluene (2×40 mL). The organic extracts were combined, washed with diluted HCl (10%, 50 mL), water (50 mL) and saturated brine (50 mL). The solution was then dried with magnesium sulfate (5 g) with stirring at RT for 1 hour. The solution was passed through a short Silica gel column eluted with toluene. The solvent was removed by rotary evaporation and the crude product was crystallized from toluene/ethanol to give 2.36 g of light-yellow solid material. Further purification with preparative chromatography generated 1.5 g product in 99.9% purity by UPLC analysis. The structure was confirmed by NMR analysis.

Synthesis Example 3

This example illustrates the synthesis of a compound having Formula I, Compound E1.

3,8-di([1,1':3',1''-terphenyl]-3-yl)-fluoranthene

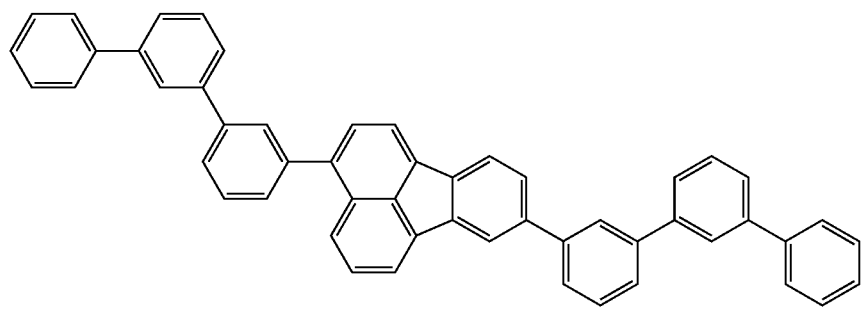 [SMILES: c1ccc(-c2cccc(-c3cccc(-c4ccc5c(c4)-c4cccc6c(-c7cccc(-c8cccc(-c9ccccc9)c8)c7)ccc-5c46)c3)c2)cc1]

Step a. 3,8-dibromofluoranthene

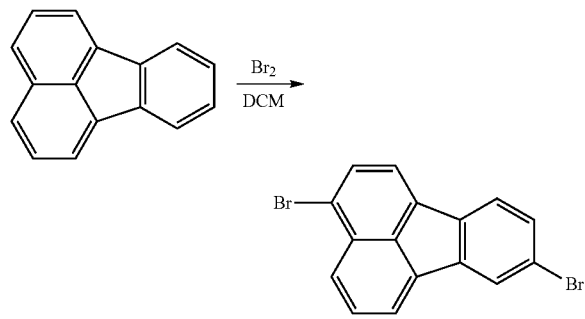

To a 500 mL round bottom flask equipped with stir bar and reflux condenser were added fluoranthene (15.00 g, 74.16 mmol) and DCM (100 mL). Bromine (11.85 g, 74.16 mmol) in DCM (50 mL) was added slowly over 20 minutes. Reaction was shown by UPLC to have 14% of fluoranthene, 74% of 7-bromofluoranthene, and 9% of 3,8-dibromofluoranthene. More bromine (11.85 g, 74.16 mmol) in DCM (50 mL) was added in 10 minutes with the reaction mixture cooled with an ice water bath. Reaction was shown 75% of 3,8-dibromofluoranthene formation by UPLC after 2 hours. More bromine (2.96 g, 18.61 mmol) in DCM (10 mL) was added to the chilled reaction. Reaction was then stirred at ambient temperature overnight. The solvent was removed and the residue was dissolved in toluene (500 mL) under heating, treated with sodium thiosulfate (10% aq, 200 mL), and allowed to cool. The product crystallized out of the organic layer was collected and rinsed with methanol (5.36 g, 99% pure). The organic layer was then separated and repeatedly recrystallized from toluene (200 mL) under heating. To give more products with varies purities, 3.34 g, 97% pure, 6.41 g, 90% pure, 6.48 g, 85% pure and 1.5.0 g, 70% pure. The product structure was confirmed by NMR and X-Ray crystallography analysis.

Step b. 3,8-di([1,1':3',1''-terphenyl]-3-yl)-8-phenyl-fluoranthene

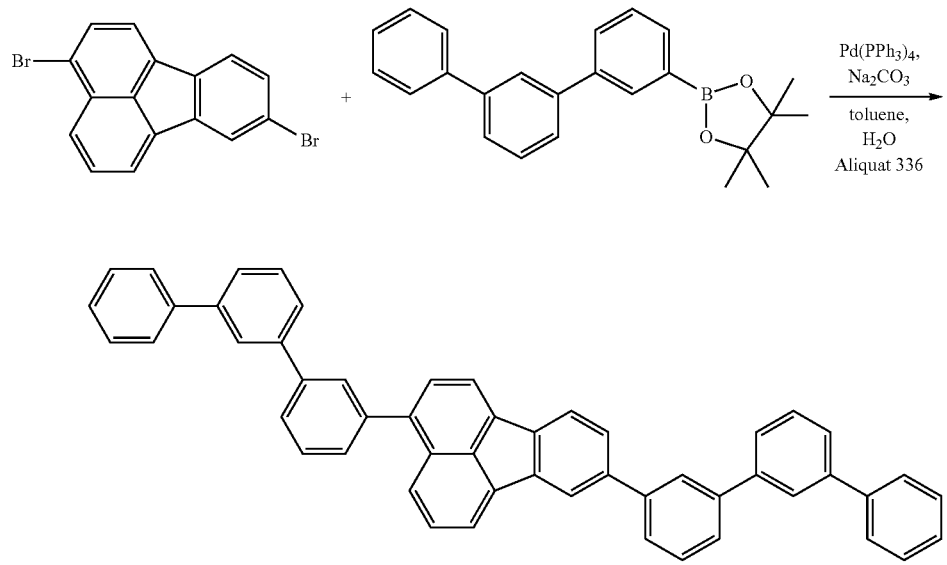

To a 500 mL RB flask equipped with an magnetic stirrer and a condenser which was attached to a nitrogen line, were added 3,8-dibromofluoranthene (2.80 g, 7.67 mmol), 2-([1,1':3',1"-terphenyl]-3-yl)-4,4,5,5-tetramethyl-1,3,2-dioxaborolane (6.00 g, 16.17 mmol), sodium carbonate (2 M, 20 mL), Aliquat 336 (0.5 g) and toluene (200 mL). The mixture was bubbled with nitrogen for 15 min. Tetrakis(triphenylphospine)palladium (89 mg, 0.08 mmol) was then added and the system was purged for another 15 min. The reaction mixture was stirred and refluxed in a heating block at 97° C. under nitrogen overnight. After cooling down to RT, the organic phase was separated, washed with diluted HCl (10%, 100 mL), water (100 mL) and saturated brine (100 mL). The solution was then dried with magnesium sulfate, passed through a Silica gel plug eluted with toluene. The volume of the solution was reduced to 200 mL and the solution was allowed to stand at ambient temperature overnight. Crystals were collected and rinsed with toluene and methanol. The crude product was recrystallized from toluene and ethanol to give 4.9 g of light yellow material. Further purification by repeated crystallization from toluene and ethanol gave 880 mg of product in 99.85% purity). The structure was confirmed by NMR analysis.

Synthesis Example 4

This example illustrates the synthesis of a compound having Formula III, Compound E21.

3-(3-(6-(9,9-di-p-tolyl-9H-fluoren-2-yl)naphthalen-2-yl)phenyl)fluoranthene

Step a. 6-(9,9-di-p-tolyl-9H-fluoren-2-yl)naphthalen-2-ol

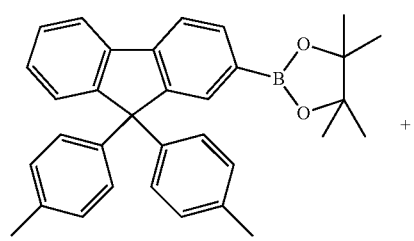

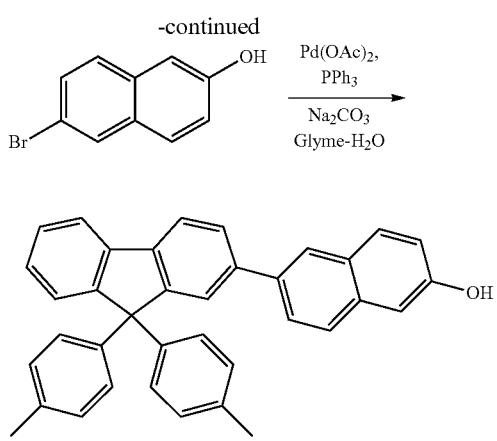

A 1 L 3-neck round-bottomed flask equipped with a condenser, thermometer and side arm stopper was charged with a suspension 6-bromonaphthalen-2-ol (4.46 g, 20 mmol), 2-(9,9-di-p-tolyl-9H-fluoren-2-yl)-4,4,5,5-tetramethyl-1,3,2-dioxaborolane (9.45 g, 20 mmol, 100 mol %) in 1,2-dimethoxyethane (120 mL) and sodium carbonate (2 M, 30 mL). The mixture was purged with nitrogen for 10 minutes, then palladium acetate (90 mg, 0.4 mmol, 2.0 mol %) and triphenylphosphine (210 mg, 0.8 mmol, 4 mol %) were added. The reaction mixture was heated to reflux (Tex=85° C.) and stirred under nitrogen overnight. After which, the reaction mixtures was allowed cool to ambient temperature, then to −5° C. in a refrigerator (4 hr). During the time, some solid material was formed. The solid was filtered, washed with water and dried in air. The crude product was dissolved in DCM (200 mL) and the solution was washed with diluted HCl (10%, 60 mL), water (60 mL) and brine (60 mL). The solution was dried over $MgSO_4$, filtered and concentrated to a light-brown soft solid material. The material was separated on silica gel column, eluted with 1/3 DCM in hexanes first, then with DCM. The separation was monitored by TLC (DCM/Hexane 1/3) and the product containing fractions were combined. The solvent was removed by rotary evaporation and the residue was crystallized from DCM/acetonitrile to give a white crystalline material (7.63 g, 78%) having a purity of 98% based on UPLC analysis. NMR spectra are consistent with the structure of the product.

Step b. 6-(9,9-di-p-tolyl-9H-fluoren-2-yl)naphthalen-2-yl trifluoromethanesulfonate

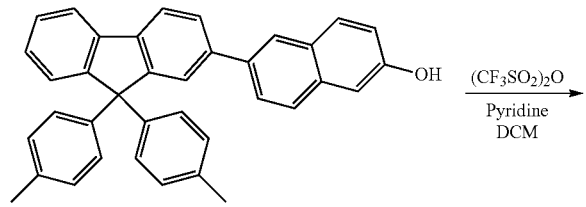

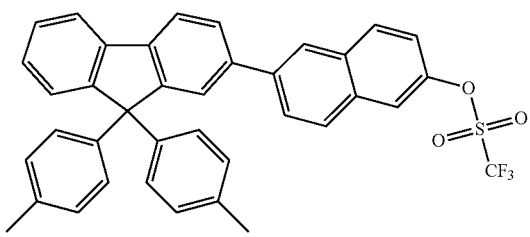

To a 500 mL 3-necked RB flask equipped with a magnetic stirrer an addition funnel in a water bath, were added 6-(9,9-di-p-tolyl-9H-fluoren-2-yl)naphthalen-2-ol (7.60 g, 15.55 mmol), DCM (90 mL) and pyridine (3.0 mL).* With stirring, trifluoromethane sulfonic anhydride (4.8 mL, 17.11 mmol) in DCM (10 mL) was added dropwise (fuming) in 5 min. After which, the reaction was stirred at ambient temperature for 1 hr. The reaction was quenched by adding water (50 mL) slowly. The organic layer was separated, washed with diluted HCl (10%, 2×50 mL), water (50 mL) and saturated brine (50 mL). The solution was then stirred with $MgSO_4$ (10 g) at ambient temperature for 1 hour. The mixture was filtered through a Silica gel plug (5 cm) eluted with DCM. The solvent was removed by rotary evaporation and the residue was crystallized from hexane. The product was obtained as a light orange crystalline material with 8.6 g yield (89%) in a purity of 97.5% by HPLC analysis. NMR analysis indicated the product is consistent with the structure expected.

Step c. 2-(6-(9,9-di-p-tolyl-9H-fluoren-2-yl)naphthalen-2-yl)-4,4,5,5-tetramethyl-1,3,2-dioxaborolane

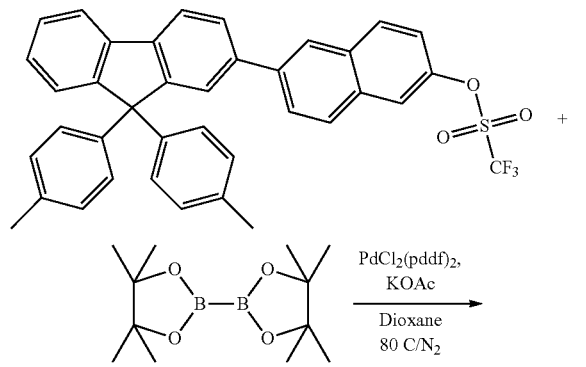

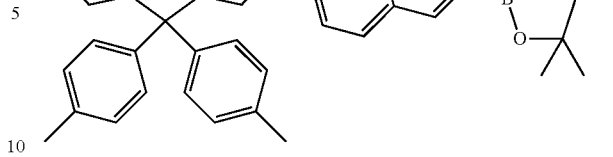

To a 500 mL RB flask equipped with an magnetic stirrer and a condenser which was attached to a nitrogen line, were added 6-(9,9-di-p-tolyl-9H-fluoren-2-yl)naphthalen-2-yl trifluoromethanesulfonate (8.60 g, 13.51 mmol), 4,4,4',4',5,5,5',5'-octamethyl-2,2'-bi(1,3,2-dioxaborolane (4.11 g, 16.21 mmol), potassium acetate 3.98 g, 40.53 g mmol), and dioxane (130 mL).

The mixture was bubbled with nitrogen while the system was purged with nitrogen for 15 min. $Pd(dppf)_2Cl_2$ (327 mg, 0.40 mmol). After which, the mixture was stirred and heated with a heating mantle at 80° C. under nitrogen overnight. The original light brown color turned to dark within 20 min of reaction. After cooling, some solid was observed. The volume of the mixture was reduced to about 15 mL on rotavap and water (100 mL) was added and the mixture was allowed to stand at RT for 1 hr. The solid formed was filtered and washed with water. The crude product was re-dissolved in DCM (150 mL), washed with saturated brine (80 mL) and dried with $MgSO_4$ (10 g). The solution was passed through a short Silica gel column eluted with DCM. The product containing fractions were combined, and the solvent was removed by rotary evaporation. The residual solid was crystallized from hexane to give the product as a light orange crystalline material. Yield, 7.11 g (88%). Purity, 95.5% by UPLC. NMR spectra are in consistent with the structure expected. 3-(3-bromophenyl)fluoranthene.

Step d. 3-(3-bromophenyl)fluroanthene

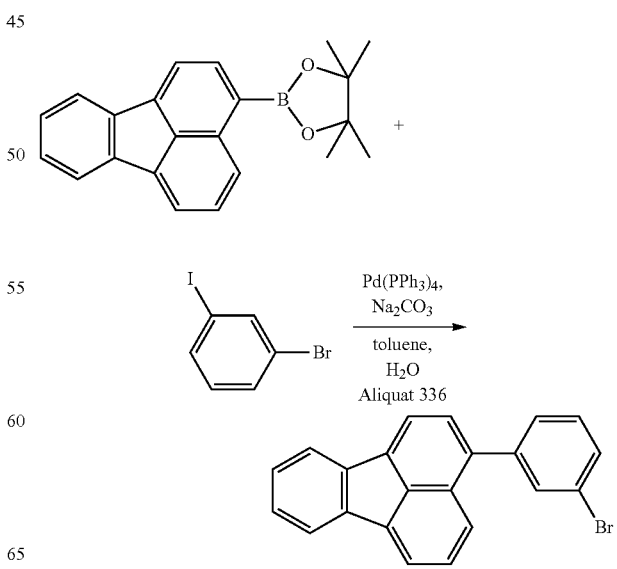

To a 500 mL RB flask equipped with an magnetic stirrer and a condenser which was attached to a nitrogen line, were added 1-bromo-3-iodobenzene (8.08 g, 28.56 mmol), 2-(fluoranthen-3-yl)-4,4,5,5-tetramethyl-1,3,2-dioxaborolane (9.19 g, 28.00 mmol), sodium carbonate (2 M, 42 mL) and toluene (168 mL). The mixture was bubbled with nitrogen for 15 min. Tetrakis(triphenylphospine)palladium (323 mg, 0.28 mmol). was then added and the system was purged for another 15 min. The reaction mixture was stirred and refluxed in a heating block at 97° C. under nitrogen for 22 hr. During the time the reaction solution maintained a light-brown color. UPLC analysis indicated that the reaction was complete. More Pd catalyst (70 mg) and 1-bromo-3-iodobenzene (1.0 g) were added and the reaction was continued overnight. After cooling to RT, the organic phase was separated and the aqueous layer was extracted with toluene (2×40 mL). The organic extracts were combined, washed with diluted HCl (10%, 100 mL), water (100 mL) and saturated brine (100 mL). The solution was then dried with magnesium sulfate (15 g) with stirring at RT for 1 hour. The mixture was filtered, and the solvent was removed by rotary evaporation. The residue was separated on Silica gel column, eluted with hexane first then with DCM/hexane (1/1). The product containing fractions were combined and the solvent was evaporated. The crude product was crystallized from hexane and dried in vacuum oven at RT overnight to give 5.5 g of pale yellow crystalline material in purity of 97% by UPLC analysis. NMR spectra are in consistent with the structure expected.

Step e. 3-(3-(6-(9,9-di-p-tolyl-9H-fluoren-2-yl)naphthalen-2-yl)phenyl)fluoranthene

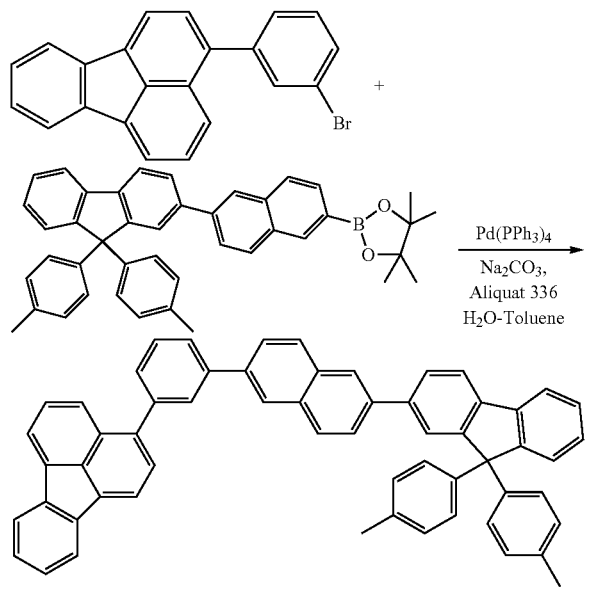

To a 500 mL RB flask equipped with an magnetic stirrer and a condenser which was attached to a nitrogen line, were added 3-(3-bromophenyl)fluroanthene (2.86 g, 8.01 mmol), 2-(6-(9,9-di-p-tolyl-9H-fluoren-2-yl)naphthalen-2-yl)-4,4,5,5-tetramethyl-1,3,2-dioxaborolane (4.80 g, 8.01 mmol). Sodium carbonate (2 M, 16 mL) and toluene (100 mL). The mixture was bubbled with nitrogen for 15 min. Tetrakis(triphenylphospine)palladium (139 mg, 0.28 mmol) was then added. The reaction mixture was stirred and refluxed in a heating block at 97° C. under nitrogen for 18 hr. During the time the reaction solution maintained a light-brown color. UPLC analysis indicated that the reaction was complete. After cooling to RT, some precipitate was observed. The solid was filtered and the filtrate was concentrated on rotavap to give more solid. The solids were combined, washed with water first and then with ethanol, and dried in air. The solid was re-dissolved in toluene (200 mL) with heating. While still warm, the solution was passed through a Silica gel plug eluted with toluene. The volume of toluene solution was reduced by rotary evaporation and ethanol was added to the residue. The crude product was collected and further purified on a Silica gel column to give a light yellow crystalline material, 4.50 g (67.5%) in 99.9% purity by UPLC analysis. NMR spectra are in consistent with the structure expected.

Device Examples

These examples demonstrate the fabrication and performance of OLED devices.
(1) Materials
HIJ-1 is an electrically conductive polymer doped with a polymeric fluorinated sulfonic acid.
HT-1 is a triarylamine polymer.
HT-2 is a triarylamine polymer.
HT-3 is a bi-naphthyl diamine polymer.
Host-1 is a deuterated 9,10-diarylanthracene compound.
Host-2 is a deuterated diaryl-binaphthyl compound
Dopant-1 is bis(diarylamino)chrysene compound.
Dopant-2 is a deuterated bis(diarylamino)chrysene compound.
Dopant-3 is the same as Dopant-2 but with a higher degree of deuteration.
Dopant-4 is a bis(diarlyamino)benzofluorene compound.
EIJ-1 is a quinolate compound.
(2) Device Fabrication
OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission.

The patterned ITO substrates were cleaned and spin-coated with an aqueous dispersion of HIJ-1. The first and second hole transport layers were sequentially formed by spin-coating HT-1 and HT-2, respectively, from solvent solutions. The workpieces were then spin-coated with a solution of the photoactive layer materials in methyl benzoate and heated to remove solvent. The workpieces were masked and placed in a vacuum chamber. A layer of electron transport material was deposited by thermal evaporation, followed by a layer of EIJ-1. Masks were then changed in vacuo and a layer of Al was deposited by thermal evaporation. The chamber was vented, and the devices were encapsulated using a glass lid, desiccant, and UV curable epoxy.
(3) Device Characterization
The OLED samples were characterized by measuring their (1) current-voltage (I-V) curves, (2) electroluminescence luminance versus voltage, and (3) electroluminescence spectra versus voltage. All three measurements were performed at the same time and controlled by a computer. The current efficiency of the device at a certain voltage is determined by dividing the electroluminescence luminance of the LED by the current density needed to run the device.

The unit is a cd/A. The color coordinates were determined using either a Minolta CS-100 meter or a Photoresearch PR-705 meter. Current density is given in mA/cm$^2$.

Example 1

This example illustrates the use of a compound having Formula I as an electron transport material in a device.

The device had the following structure on a glass substrate:
anode=ITO (50 nm)
hole injection layer=HIJ-1 (100 nm)
hole transport layer=HT-1 (4 nm)
hole transport layer=HT-2 (96 nm)
photoactive layer, discussed below (40 nm)
electron transport layer, discussed below (20 nm)
electron injection layer/cathode=EIJ-1/Al (3.5/100 nm)
The photoactive layer contained Host-1 and Dopant-1 in a weight ratio of 93:7.

The electron transport layer was Compound E8.

The results are given in Table 1.

Example 2

This example illustrates the use of a compound having Formula I as an electron transport material and as a cohost in a photoactive layer.

The device had the following structure on a glass substrate:
anode=ITO (50 nm)
hole injection layer=HIJ-1 (100 nm)
hole transport layer=HT-1 (4 nm)
hole transport layer=HT-2 (96 nm)
photoactive layer, discussed below (40 nm)
electron transport layer, discussed below (20 nm)
electron injection layer/cathode=EIJ-1/Al (3.5/100 nm)
The photoactive layer contained Host-1:Compound E8:Dopant-2 in a ratio of 83:10:7, by weight.
The electron transport layer was Compound E8.
The results are given in Table 1.

TABLE 1

Device results

| Example | CE (cd/A) | EQE (%) | Voltage @ 15 mA/cm2 (V) | CIE (x, y) | T70, hrs | Lifetime test luminance (nits) |
|---|---|---|---|---|---|---|
| 1 | 5.5 | 6.2 | 5.8 | 0.137 0.101 | 1480 | 1246 |
| 2 | 3.6 | 5.0 | 4.8 | 0.145 0.076 | 90 | 914 |

All data @ 1000 nits unless otherwise specified. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 23 mA/cm$^2$ and 50° C.

Examples 3 and 4

These examples illustrate the use of a compound having Formula I as an electron transport material.

The devices had the following structure on a glass substrate:
anode=ITO (50 nm)
hole injection layer=HIJ-1 (50 nm)
hole transport layer=HT-3 (4 nm)
hole transport layer=HT-2 (14 nm)
photoactive layer=Host-1:Host-2:Dopant-3 in 73:20:7 weight ratio (40 nm)
electron transport layer, discussed below (10 nm)
electron injection layer/cathode=CsF/Al (7/100 nm)

In Example 3, the electron transport material was Compound E3.

In Example 4, the electron transport material was Compound E1.

The results are given in Table 2.

TABLE 2

Device results

| Ex. | Electron Transport Layer | CE (cd/A) | EQE (%) | Voltage @ 15 mA/cm2 (V) | CIE (x, y) | T70, hrs | Lifetime test current density | Lifetime test luminance (nits) |
|---|---|---|---|---|---|---|---|---|
| 3 | Comp. E3 | 3.8 | 4.9 | 5.3 | 0.143 0.085 | 500 | 25 | 1034 |
| 4 | Comp. E1 | 3.5 | 4.6 | 5.1 | 0.144 0.083 | 600 | 28 | 992 |

All data @ 1000 nits unless otherwise specified. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 50° C.

Example 5

This example illustrates the use of a compound having Formula I as a host in a photoactive layer and a different compound having Formula I as an electron transport material in the electron transport layer.

The device had the following structure on a glass substrate:
anode=ITO (50 nm)
hole injection layer=HIJ-1 (100 nm)
hole transport layer=HT-1 (4 nm)
hole transport layer=HT-2 (96 nm)

photoactive layer=Compound E3 host and Dopant-4 in 93:7 weight ratio (40 nm)
electron transport layer: Compound E8 (20 nm)
electron injection layer/cathode=EIJ-1/Al (3.5/100 nm)
The results are given in Table 3.

TABLE 3

Device results

| Example | CE (cd/A) | EQE (%) | Voltage @ 15 mA/cm2 (V) | CIE (x, y) | T70, hrs | Lifetime test luminance (nits) |
|---|---|---|---|---|---|---|
| 5 | 3.3 | 3.5 | 4.6 | 0.145 0.105 | 50 | 1320 |

All data @ 1000 nits unless otherwise specified. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 23 mA/cm2 and 50° C.

Example 6

This example illustrates the use of a compound having Formula III as an electron transport material in a device.
The devices had the following structure on a glass substrate:
  anode=ITO (50 nm)
  hole injection layer=HIJ-1 (50 nm)
  hole transport layer=HT-3 (4 nm)
  hole transport layer=HT-2 (14 nm)
  photoactive layer=Host-1:Host-2:Dopant-3 in 73:20:7 weight ratio (40 nm)
  electron transport layer, Compound E21 (10 nm)
  electron injection layer/cathode=CsF/Al (7/100 nm)
The results are given in Table 4.

TABLE 4

Device results

| Ex. | CE (cd/A) | EQE (%) | Voltage @ 15 mA/cm2 (V) | CIE (x, y) | T70 hrs | Lifetime test current density | Lifetime test luminance (nits) |
|---|---|---|---|---|---|---|---|
| 6 | 3.8 | 4.9 | 5.5 | 0.144 0.086 | 700 | 27.5 | 1046 |

All data @ 1000 nits unless otherwise specified. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 50° C.

Example 7

This example illustrates the use of a compound having Formula III as a host in the photoactive layer of a device, and a compound having Formula I as the electron transport material.
The device had the following structure on a glass substrate:
  anode=ITO (50 nm)
  hole injection layer=HIJ-1 (100 nm)
  hole transport layer=HT-1 (4 nm)
  hole transport layer=HT-2 (96 nm)
  photoactive layer=Compound E21 host and Dopant-4 in 93:7 weight ratio (40 nm)
  electron transport layer: Compound E8 (20 nm)
  electron injection layer/cathode=EIJ-1/Al (3.5/100 nm)
The results are given in Table 5.

TABLE 5

Device results

| Ex. | CE (cd/A) | EQE (%) | Voltage @ 15 mA/cm2 (V) | CIE (x, y) | T70, hrs | Lifetime test current density | Lifetime test luminance (nits) |
|---|---|---|---|---|---|---|---|
| 7 | 3.9 | 4.0 | 4.7 | 0.146 0.111 | 64 | 23 | 1320 |

All data @ 1000 nits unless otherwise specified. CE is the current efficiency; EQE is the external quantum efficiency; CIE(x,y) are the x and y color coordinates according to the C.I.E. chromaticity scale (Commission Internationale de L'Eclairage, 1931); T70 is the time, in hours, to reach 70% of the initial luminance at 50° C.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:
1. An electroactive material having Formula I

Formula I

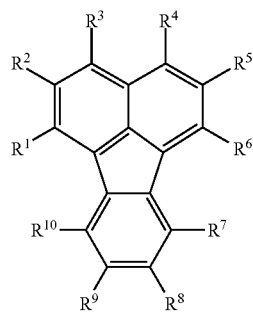

wherein:
R$^1$-R$^{10}$ are the same or different and are selected from the group consisting of H, D, alkyl, silyl, aryl, deuterated alkyl, deuterated silyl, and deuterated aryl;
with the proviso that no more than one of R$^1$-R$^{10}$ is biphenyl and at least one of R$^1$-R$^6$ and at least one of R$^7$-R$^{10}$ have Formula II

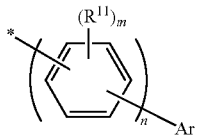

Formula II wherein:
Ar is selected from the group consisting of S-heteroaryl, N,O-heteroaryl, N,S-heteroaryl, spirofluorenyl, and deuterated analogs thereof;
R$^{11}$ is the same or different at each occurrence and is selected from the group consisting of D, alkyl, silyl, aryl, deuterated alkyl, deuterated silyl, and deuterated aryl, wherein adjacent R$^{11}$ groups can join to form a fused aromatic ring or fused deuterated aromatic ring;
m is an integer from 0-4; and
n is an integer from 1-5.

2. The electroactive material of claim 1, wherein at least two of R$^7$-R$^{10}$ have Formula II.

3. The electroactive material of claim 1, wherein Ar is an N,O-heteroaryl selected from the group consisting of oxazole, benzoxazole, and deuterated analogs thereof.

4. The electroactive material of claim 1, wherein Ar is an N,S-heteroaryl selected from the group consisting of thiazole, benzothiazole, and deuterated analogs thereof.

5. An electronic device comprising at least one electroactive layer positioned between two electrical contact layers, wherein the at least one electroactive layer comprises the electroactive material having Formula I according to claim 1.

6. The device of claim 5, comprising an anode, a hole transport layer, a photoactive layer, an electron transport layer, and a cathode, wherein at least one of the photoactive layer and the electron transport layer comprises the electroactive material having Formula I.

7. The device of claim 5, wherein the photoactive layer comprises (a) a host material which is the electroactive material having Formula I and (b) an organometallic electroluminescent dopant.

8. The device of claim 5, wherein the electron transport layer comprises the electroactive material having Formula I.

9. An electroactive material having Formula I

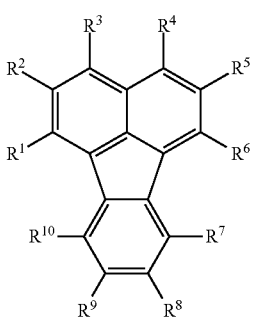

Formula I wherein:
R$^1$-R$^{10}$ are the same or different and are selected from the group consisting of H, D, alkyl, silyl, aryl, deuterated alkyl, deuterated silyl, and deuterated aryl;
with the proviso that no more than one of R$^1$-R$^{10}$ is biphenyl and at least two of R$^1$-R$^{10}$ have Formula II

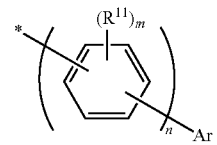

Formula II wherein:
Ar is an S-heteroaryl selected from the group consisting of thiophene, (di)benzothiophene, thienothiophene, and deuterated analogs thereof;
R$^{11}$ is the same or different at each occurrence and is selected from the group consisting of D, alkyl, silyl, aryl, deuterated alkyl, deuterated silyl, and deuterated aryl, wherein adjacent R$^{11}$ groups can join to form a fused aromatic ring or fused deuterated aromatic ring;
m is an integer from 0-4; and
n is an integer from 1-5.

10. An electronic device comprising at least one electroactive layer positioned between two electrical contact layers, wherein the at least one electroactive layer comprises the electroactive material having Formula I according to claim 9.

11. The device of claim 10, comprising an anode, a hole transport layer, a photoactive layer, an electron transport layer, and a cathode, wherein at least one of the photoactive layer and the electron transport layer comprises the electroactive material having Formula I.

12. The device of claim 10, wherein the photoactive layer comprises (a) a host material which is the electroactive material having Formula I and (b) an organometallic electroluminescent dopant.

13. The device of claim 10, wherein the electron transport layer comprises the electroactive material having Formula I.

14. An electroactive material having Formula I

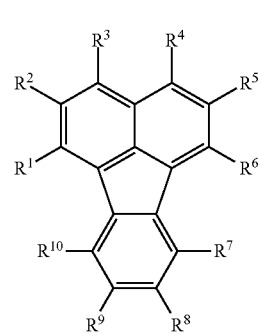

Formula I wherein:
R$^1$-R$^{10}$ are the same or different and are selected from the group consisting of H, D, alkyl, silyl, aryl, deuterated alkyl, deuterated silyl, and deuterated aryl;
with the proviso that no more than one of R$^1$-R$^{10}$ is biphenyl and at least two of R$^1$-R$^{10}$ have Formula II Formula II

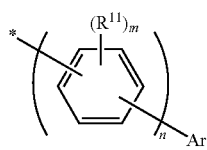

wherein:
Ar is selected from the group consisting of spirofluorenyl and a deuterated analog thereof;
$R^{11}$ is the same or different at each occurrence and is selected from the group consisting of D, alkyl, silyl, aryl, deuterated alkyl, deuterated silyl, and deuterated aryl, wherein adjacent $R^{11}$ groups can join to form a fused aromatic ring or fused deuterated aromatic ring;
m is an integer from 0-4; and
n is an integer from 1-5.

15. The electroactive material of claim 14, wherein Ar is selected from the group consisting of

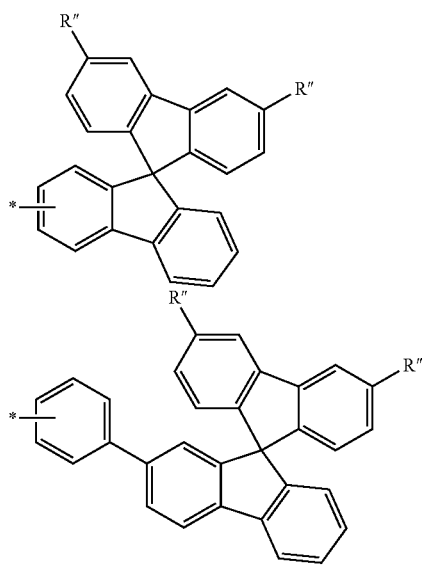

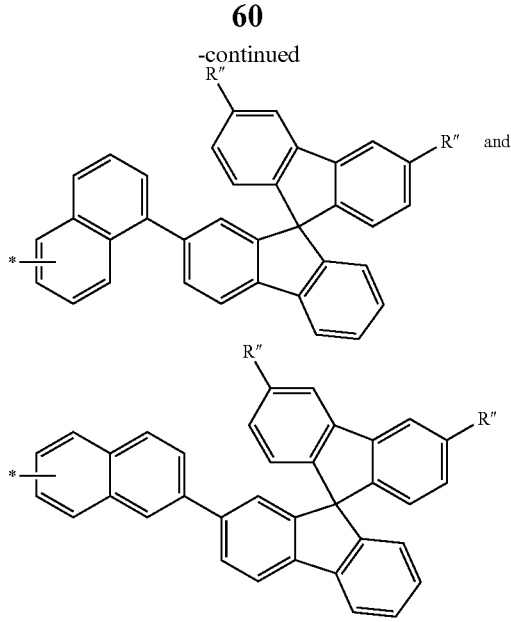

where:
R″ is the same or different at each occurrence and is selected from the group consisting of H, D, $C_{1-12}$ alkyl, and deuterated $C_{1-12}$ alkyl, and positions available for H can be H or D, and
* indicates a point of attachment.

16. An electronic device comprising at least one electroactive layer positioned between two electrical contact layers, wherein the at least one electroactive layer comprises the electroactive material having Formula I according to claim 14.

17. The device of claim 16, comprising an anode, a hole transport layer, a photoactive layer, an electron transport layer, and a cathode, wherein at least one of the photoactive layer and the electron transport layer comprises the electroactive material having Formula I.

18. The device of claim 16, wherein the photoactive layer comprises (a) a host material which is the electroactive material having Formula I and (b) an organometallic electroluminescent dopant.

19. The device of claim 16, wherein the electron transport layer comprises the electroactive material having Formula I.

* * * * *